(12) United States Patent
Kokish et al.

(10) Patent No.: US 9,408,669 B2
(45) Date of Patent: Aug. 9, 2016

(54) ACTIVE DRIVE MECHANISM WITH FINITE RANGE OF MOTION

(71) Applicant: Hansen Medical, Inc., Mountain View, CA (US)

(72) Inventors: Arkady Kokish, Los Gatos, CA (US); J. Scot Hart, Menlo Park, CA (US); Alan Yu, Union City, CA (US); Enrique Romo, Dublin, CA (US)

(73) Assignee: HANSEN MEDICAL, INC., Mountain View, CA (US)

( * ) Notice: Subject to any disclaimer, the term of this patent is extended or adjusted under 35 U.S.C. 154(b) by 575 days.

(21) Appl. No.: 13/838,777

(22) Filed: Mar. 15, 2013

(65) Prior Publication Data

US 2014/0276939 A1     Sep. 18, 2014

(51) Int. Cl.
*A61M 25/01* (2006.01)
*A61B 19/00* (2006.01)
*A61B 17/00* (2006.01)

(52) U.S. Cl.
CPC ....... *A61B 19/2203* (2013.01); *A61B 17/00234* (2013.01); *A61M 25/0113* (2013.01)

(58) Field of Classification Search
CPC ........... A61B 17/0057; A61B 17/0643; A61B 17/6408; A61B 17/66; A61B 17/00234; F16L 1/20; F16L 1/09; B25B 1/2484; B25B 1/22; B25B 27/10; B25B 27/16; B25B 27/00; B25B 5/087
See application file for complete search history.

(56) References Cited

U.S. PATENT DOCUMENTS

| 3,835,854 A | 9/1974 | Jewett |
| 4,945,305 A | 7/1990 | Blood |
| 5,078,714 A | 1/1992 | Katims |
| 5,339,799 A | 8/1994 | Kami et al. |
| 5,341,807 A | 8/1994 | Nardella |

(Continued)

FOREIGN PATENT DOCUMENTS

| CA | 2285342 A1 | 10/1998 |
| EP | 2567670 | 3/2013 |

(Continued)

OTHER PUBLICATIONS

European Search Report for European Patent Application No. 14160078.3 dated Feb. 11, 2015. (6 pages).

(Continued)

*Primary Examiner* — Monica Carter
*Assistant Examiner* — Seahee Yoon
(74) *Attorney, Agent, or Firm* — Dorsey & Whitney LLP; Scott M. Smith

(57) ABSTRACT

Various exemplary drive apparatuses and associated methods are disclosed for driving an elongated member, e.g., a catheter, sheath, or guidewire. An exemplary drive apparatus may include a first component and a moveable component, each configured to selectively grip the elongated member. In some examples, the first and moveable components may each include a gripping device. The moveable component may be configured to selectively move axially and rotationally with respect to a support surface to effect axial movement and rotation movement, respectively, of the elongated member with respect to the support surface within a range of motion of the moveable component. The moveable component may be configured to move the elongated member across a predetermined movement having a magnitude greater than the range of motion.

18 Claims, 13 Drawing Sheets

(56) References Cited

U.S. PATENT DOCUMENTS

| | | | |
|---|---|---|---|
| 5,368,015 A | 11/1994 | Wilk | |
| 5,394,875 A | 3/1995 | Lewis et al. | |
| 5,397,443 A | 3/1995 | Michaels | |
| 5,398,691 A | 3/1995 | Martin et al. | |
| 5,408,409 A | 4/1995 | Glassman et al. | |
| 5,447,529 A | 9/1995 | Marchlinski et al. | |
| 5,469,857 A | 11/1995 | Laurent et al. | |
| 5,477,856 A | 12/1995 | Lundquist | |
| 5,492,131 A | 2/1996 | Galel | |
| 5,524,180 A | 6/1996 | Wang et al. | |
| 5,600,330 A | 2/1997 | Blood | |
| 5,631,973 A | 5/1997 | Green | |
| 5,662,108 A | 9/1997 | Budd et al. | |
| 5,673,704 A | 10/1997 | Marchlinski et al. | |
| 5,697,377 A | 12/1997 | Wittkampf | |
| 5,713,946 A | 2/1998 | Ben-Haim | |
| 5,722,959 A | 3/1998 | Bierman | |
| 5,738,096 A | 4/1998 | Ben-Haim | |
| 5,749,362 A | 5/1998 | Funda et al. | |
| 5,754,741 A | 5/1998 | Wang et al. | |
| 5,762,458 A | 6/1998 | Wang et al. | |
| 5,779,623 A | 7/1998 | Bonnell | |
| 5,784,542 A | 7/1998 | Ohm et al. | |
| 5,799,055 A | 8/1998 | Peshkin et al. | |
| 5,815,640 A | 9/1998 | Wang et al. | |
| 5,825,982 A | 10/1998 | Wright et al. | |
| 5,833,608 A | 11/1998 | Acker | |
| 5,836,869 A | 11/1998 | Kudo et al. | |
| 5,836,874 A | 11/1998 | Swanson et al. | |
| 5,836,990 A | 11/1998 | Li | |
| 5,843,076 A | 12/1998 | Webster, Jr. et al. | |
| 5,845,646 A | 12/1998 | Lemelson | |
| 5,859,934 A | 1/1999 | Green | |
| 5,876,325 A | 3/1999 | Mizuno et al. | |
| 5,878,193 A | 3/1999 | Wang et al. | |
| 5,891,095 A | 4/1999 | Eggers et al. | |
| 5,925,078 A | 7/1999 | Anderson | |
| 5,935,079 A | 8/1999 | Swanson et al. | |
| 5,950,629 A | 9/1999 | Taylor et al. | |
| 5,951,475 A | 9/1999 | Gueziec et al. | |
| 5,953,683 A | 9/1999 | Hansen et al. | |
| 5,983,126 A | 11/1999 | Wittkampf | |
| 6,004,271 A | 12/1999 | Moore | |
| 6,061,587 A | 5/2000 | Kucharczyk et al. | |
| 6,063,022 A | 5/2000 | Ben-Haim | |
| 6,063,095 A | 5/2000 | Wang et al. | |
| 6,080,181 A | 6/2000 | Jensen et al. | |
| 6,083,170 A | 7/2000 | Ben-Haim | |
| 6,096,004 A | 8/2000 | Meglan et al. | |
| 6,106,511 A | 8/2000 | Jensen | |
| 6,129,668 A | 10/2000 | Haynor et al. | |
| 6,132,368 A | 10/2000 | Cooper | |
| 6,161,032 A | 12/2000 | Acker | |
| 6,171,234 B1 | 1/2001 | White et al. | |
| 6,172,499 B1 | 1/2001 | Ashe | |
| 6,203,493 B1 | 3/2001 | Ben-Haim | |
| 6,226,543 B1 | 5/2001 | Gilboa et al. | |
| 6,228,028 B1 | 5/2001 | Klein et al. | |
| 6,233,476 B1 | 5/2001 | Strommer et al. | |
| 6,233,504 B1 | 5/2001 | Das et al. | |
| 6,246,200 B1 | 6/2001 | Blumenkranz et al. | |
| 6,259,806 B1 | 7/2001 | Green | |
| 6,266,551 B1 | 7/2001 | Osadchy et al. | |
| 6,272,371 B1 | 8/2001 | Shlomo | |
| 6,301,496 B1 | 10/2001 | Reisfeld | |
| 6,309,397 B1 | 10/2001 | Julian et al. | |
| 6,310,828 B1 | 10/2001 | Mumm et al. | |
| 6,312,435 B1 | 11/2001 | Wallace et al. | |
| 6,331,181 B1 | 12/2001 | Tierney et al. | |
| 6,363,279 B1 | 3/2002 | Ben-Haim et al. | |
| 6,370,411 B1 | 4/2002 | Osadchy et al. | |
| 6,371,952 B1 | 4/2002 | Madhani et al. | |
| 6,375,471 B1 | 4/2002 | Wendlandt et al. | |
| 6,380,732 B1 | 4/2002 | Gilboa | |
| 6,381,483 B1 | 4/2002 | Hareyama et al. | |
| 6,384,483 B1 | 5/2002 | Igarashi et al. | |
| 6,393,340 B2 | 5/2002 | Funda et al. | |
| 6,398,731 B1 | 6/2002 | Mumm et al. | |
| 6,400,979 B1 | 6/2002 | Stoianovici et al. | |
| 6,415,171 B1 | 7/2002 | Gueziec et al. | |
| 6,424,885 B1 | 7/2002 | Niemeyer et al. | |
| 6,491,701 B2 | 12/2002 | Tierney et al. | |
| 6,493,573 B1 | 12/2002 | Martinelli et al. | |
| 6,493,608 B1 | 12/2002 | Niemeyer | |
| 6,530,913 B1 | 3/2003 | Giba et al. | |
| 6,544,230 B1 | 4/2003 | Flaherty et al. | |
| 6,550,128 B1 * | 4/2003 | Lorenz | 29/464 |
| 6,551,273 B1 | 4/2003 | Olson et al. | |
| 6,565,554 B1 | 5/2003 | Niemeyer | |
| 6,574,355 B2 | 6/2003 | Green | |
| 6,580,938 B1 | 6/2003 | Acker | |
| 6,587,750 B2 | 7/2003 | Gerbi et al. | |
| 6,594,552 B1 | 7/2003 | Nowlin | |
| 6,610,007 B2 | 8/2003 | Belson et al. | |
| 6,615,155 B2 | 9/2003 | Gilboa | |
| 6,618,612 B1 | 9/2003 | Acker et al. | |
| 6,620,173 B2 | 9/2003 | Gerbi et al. | |
| 6,626,899 B2 | 9/2003 | Houser et al. | |
| 6,629,534 B1 | 10/2003 | St. Goar et al. | |
| 6,659,939 B2 | 12/2003 | Moll et al. | |
| 6,669,709 B1 | 12/2003 | Cohn et al. | |
| 6,685,698 B2 | 2/2004 | Morley et al. | |
| 6,699,235 B2 | 3/2004 | Wallace et al. | |
| 6,716,166 B2 | 4/2004 | Govari | |
| 6,726,675 B1 | 4/2004 | Beyar | |
| 6,741,883 B2 | 5/2004 | Gildenberg | |
| 6,774,624 B2 | 8/2004 | Anderson et al. | |
| 6,783,524 B2 | 8/2004 | Anderson et al. | |
| 6,799,065 B1 | 9/2004 | Niemeyer | |
| 6,817,973 B2 | 11/2004 | Merril et al. | |
| 6,817,974 B2 | 11/2004 | Cooper et al. | |
| 6,852,107 B2 | 2/2005 | Wang et al. | |
| 6,858,003 B2 | 2/2005 | Evans et al. | |
| 6,905,460 B2 | 6/2005 | Wang et al. | |
| 6,963,792 B1 | 11/2005 | Green | |
| 7,021,173 B2 | 4/2006 | Stoianovici et al. | |
| 7,074,179 B2 | 7/2006 | Wang et al. | |
| 7,087,049 B2 | 8/2006 | Nowlin et al. | |
| 7,155,315 B2 | 12/2006 | Niemeyer et al. | |
| 7,169,141 B2 | 1/2007 | Brock et al. | |
| 7,225,012 B1 | 5/2007 | Susil et al. | |
| 7,280,863 B2 | 10/2007 | Shachar | |
| 7,297,142 B2 | 11/2007 | Brock | |
| 7,320,700 B2 | 1/2008 | Cooper et al. | |
| 7,331,967 B2 | 2/2008 | Lee et al. | |
| 7,343,195 B2 | 3/2008 | Strommer et al. | |
| 7,371,210 B2 | 5/2008 | Brock et al. | |
| 7,404,824 B1 | 7/2008 | Webler et al. | |
| 7,494,494 B2 | 2/2009 | Stoianovici et al. | |
| 7,540,866 B2 | 6/2009 | Viswanathan et al. | |
| 7,615,042 B2 | 11/2009 | Beyar et al. | |
| 7,850,642 B2 | 12/2010 | Moll et al. | |
| 7,963,288 B2 | 6/2011 | Rosenberg et al. | |
| 7,972,298 B2 | 7/2011 | Wallace et al. | |
| 7,998,020 B2 | 8/2011 | Kidd et al. | |
| 8,052,636 B2 | 11/2011 | Moll et al. | |
| 8,092,397 B2 | 1/2012 | Wallace et al. | |
| 8,126,534 B2 | 2/2012 | Maschke | |
| 8,190,238 B2 | 5/2012 | Moll et al. | |
| 8,202,244 B2 | 6/2012 | Cohen et al. | |
| 8,219,178 B2 | 7/2012 | Smith et al. | |
| 8,235,942 B2 | 8/2012 | Frassica et al. | |
| 8,244,327 B2 | 8/2012 | Fichtinger et al. | |
| 8,343,040 B2 | 1/2013 | Frassica et al. | |
| 8,498,691 B2 | 7/2013 | Moll et al. | |
| 9,023,068 B2 | 5/2015 | Viola | |
| 2001/0009976 A1 | 7/2001 | Panescu et al. | |
| 2001/0029366 A1 | 10/2001 | Swanson et al. | |
| 2002/0087169 A1 | 7/2002 | Brock et al. | |
| 2002/0138009 A1 | 9/2002 | Brockway et al. | |
| 2002/0156369 A1 | 10/2002 | Chakeres | |
| 2002/0177789 A1 | 11/2002 | Ferry et al. | |
| 2003/0050649 A1 | 3/2003 | Brock et al. | |
| 2003/0056561 A1 | 3/2003 | Butscher et al. | |

(56) References Cited

U.S. PATENT DOCUMENTS

| | | |
|---|---|---|
| 2003/0073908 A1 | 4/2003 | Desai |
| 2003/0074011 A1 | 4/2003 | Gilboa et al. |
| 2003/0109780 A1 | 6/2003 | Goste-Maniere et al. |
| 2003/0135204 A1 | 7/2003 | Lee et al. |
| 2004/0034282 A1 | 2/2004 | Quaid, III |
| 2004/0034365 A1 | 2/2004 | Lentz et al. |
| 2004/0152972 A1 | 8/2004 | Hunter |
| 2004/0171929 A1 | 9/2004 | Leitner et al. |
| 2004/0176751 A1 | 9/2004 | Weitzner et al. |
| 2004/0193146 A1 | 9/2004 | Lee et al. |
| 2004/0220588 A1 | 11/2004 | Kermode et al. |
| 2005/0027397 A1 | 2/2005 | Niemeyer |
| 2005/0059960 A1 | 3/2005 | Simaan et al. |
| 2005/0131460 A1 | 6/2005 | Gifford, III et al. |
| 2005/0159789 A1 | 7/2005 | Brockway et al. |
| 2005/0165276 A1 | 7/2005 | Belson et al. |
| 2005/0182295 A1 | 8/2005 | Soper et al. |
| 2005/0182330 A1 | 8/2005 | Brockway et al. |
| 2005/0200324 A1 | 9/2005 | Guthart et al. |
| 2005/0203382 A1 | 9/2005 | Govari et al. |
| 2006/0013523 A1 | 1/2006 | Childers et al. |
| 2006/0025676 A1 | 2/2006 | Viswanathan et al. |
| 2006/0025679 A1 | 2/2006 | Viswanathan et al. |
| 2006/0058647 A1 | 3/2006 | Strommer et al. |
| 2006/0146010 A1 | 7/2006 | Schneider |
| 2006/0178556 A1 | 8/2006 | Hasser et al. |
| 2006/0200049 A1 | 9/2006 | Leo et al. |
| 2006/0229587 A1 | 10/2006 | Beyar et al. |
| 2006/0229641 A1 | 10/2006 | Gupta et al. |
| 2006/0271036 A1 | 11/2006 | Garabedian et al. |
| 2007/0038181 A1 | 2/2007 | Melamud et al. |
| 2007/0060847 A1 | 3/2007 | Leo et al. |
| 2007/0060879 A1 | 3/2007 | Weitzner et al. |
| 2007/0065077 A1 | 3/2007 | Childers et al. |
| 2007/0123851 A1 | 5/2007 | Alejandro et al. |
| 2007/0156123 A1 | 7/2007 | Moll et al. |
| 2007/0185486 A1* | 8/2007 | Hauck et al. ................ 606/41 |
| 2007/0197939 A1 | 8/2007 | Wallace et al. |
| 2007/0249901 A1 | 10/2007 | Ohline et al. |
| 2007/0287999 A1 | 12/2007 | Malecki et al. |
| 2007/0293724 A1 | 12/2007 | Saadat et al. |
| 2007/0299434 A1 | 12/2007 | Malecki et al. |
| 2008/0009750 A1 | 1/2008 | Aeby et al. |
| 2008/0015445 A1 | 1/2008 | Saadat et al. |
| 2008/0064920 A1 | 3/2008 | Bakos et al. |
| 2008/0183071 A1 | 7/2008 | Strommer et al. |
| 2008/0300592 A1 | 12/2008 | Weitzner et al. |
| 2008/0319311 A1 | 12/2008 | Hamadeh |
| 2009/0054884 A1 | 2/2009 | Farley et al. |
| 2009/0082722 A1 | 3/2009 | Munger et al. |
| 2009/0105645 A1 | 4/2009 | Kidd et al. |
| 2009/0131872 A1 | 5/2009 | Popov |
| 2009/0137952 A1 | 5/2009 | Ramamurthy et al. |
| 2009/0221908 A1 | 9/2009 | Glossop |
| 2009/0318797 A1 | 12/2009 | Hadani |
| 2010/0081920 A1 | 4/2010 | Whitmore, III et al. |
| 2010/0130987 A1 | 5/2010 | Wenderow et al. |
| 2010/0175701 A1 | 7/2010 | Reis et al. |
| 2010/0187740 A1* | 7/2010 | Orgeron ............. B25B 5/061 269/218 |
| 2011/0015648 A1 | 1/2011 | Alvarez et al. |
| 2011/0130718 A1 | 6/2011 | Kidd et al. |
| 2012/0016346 A1 | 1/2012 | Steinmetz et al. |
| 2012/0046652 A1 | 2/2012 | Sokel |
| 2012/0245595 A1 | 9/2012 | Kesavadas et al. |
| 2012/0310112 A1 | 12/2012 | Fichtinger et al. |
| 2012/0316393 A1 | 12/2012 | Frassica et al. |
| 2013/0012779 A1 | 1/2013 | Frassica et al. |
| 2014/0276936 A1 | 9/2014 | Kokish et al. |
| 2014/0276939 A1 | 9/2014 | Kokish et al. |
| 2014/0277333 A1 | 9/2014 | Lewis et al. |
| 2014/0277334 A1 | 9/2014 | Yu et al. |
| 2015/0133858 A1 | 5/2015 | Julian et al. |

FOREIGN PATENT DOCUMENTS

| | | |
|---|---|---|
| WO | 9744089 A1 | 11/1997 |
| WO | 0011495 A1 | 3/2000 |
| WO | 0045193 A1 | 8/2000 |
| WO | 03077769 A1 | 9/2003 |
| WO | 03086190 A1 | 10/2003 |
| WO | 03091839 A2 | 11/2003 |
| WO | 2005087128 A1 | 9/2005 |
| WO | 2012037506 A2 | 3/2012 |
| WO | 2014/028702 A1 | 2/2014 |

OTHER PUBLICATIONS

Amendment and Response to Non-Final Office Action for related U.S. Appl. No. 11/678,016, filed Dec. 27, 2010 (21 pages).

European Search Report for related European Patent Application Serial No. 14160068.4, dated Feb. 6, 2015 (6 pages).

Non-Final Office Action for related application U.S. Appl. No. 11/678,016, mailed Aug. 31, 2010 (30 pages).

PCT International Preliminary Report on Patentability for International Patent Application Serial No. PCT/US2007/062617, dated Aug. 26, 2008 (7 pages).

PCT International Search Report for International Patent Application Serial No. PCT/US2006/026218, mailed Dec. 12, 2006 (2 pages).

PCT International Search Report for International Patent Application Serial No. PCT/US2005/007108, mailed Jun. 27, 2005 (4 pages).

PCT Written Opinion for International Patent Application Serial No. PCT/US2006/026218, mailed Dec. 12, 2006 (7 pages).

PCT Written Opinion for International Patent Application Serial No. PCT/US2005/007108, mailed Jun. 27, 2005 (6 pages).

\* cited by examiner

ACTIVE DRIVE MECHANISM WITH FINITE RANGE OF MOTION

BACKGROUND

Robotic interventional systems and devices are well suited for performing minimally invasive medical procedures as opposed to conventional techniques wherein the patient's body cavity is open to permit the surgeon's hands access to internal organs. However, advances in technology have led to significant changes in the field of medical surgery such that less invasive surgical procedures, in particular, minimally invasive surgery (MIS), are increasingly popular.

MIS is generally defined as a surgery that is performed by entering the body through the skin, a body cavity, or an anatomical opening utilizing small incisions rather than large, open incisions in the body. With MIS, it is possible to achieve less operative trauma for the patient, reduced hospitalization time, less pain and scarring, reduced incidence of complications related to surgical trauma, lower costs, and a speedier recovery.

Special medical equipment may be used to perform MIS procedures. Typically, a surgeon inserts small tubes or ports into a patient and uses endoscopes or laparoscopes having a fiber optic camera, light source, or miniaturized surgical instruments. Without a traditional large and invasive incision, the surgeon is not able to see directly into the patient. Thus, the video camera serves as the surgeon's eyes. The images of the interior of the body are transmitted to an external video monitor to allow a surgeon to analyze the images, make a diagnosis, visually identify internal features, and perform surgical procedures based on the images presented on the monitor.

MIS devices and techniques have advanced to the point where an insertion and rolling motion of components of an elongated component such as a catheter instrument, e.g., a catheter sheath and associated guidewire, are generally controllable by selectively operating rollers or other mechanisms for generally gripping the component. Some known mechanisms use gripping devices capable of infinite motion for insertion of a catheter, e.g., a roller, may require more complex catheter component loading procedures, or may not be compatible with replaceable components adapted for a sterile operating environment.

Accordingly, there is a need in the art for systems and methods for inserting and rolling catheter components that address or solve the above problems.

SUMMARY

Various exemplary drive apparatuses and associated methods are disclosed for driving an elongated member, e.g., a catheter, sheath, or guidewire. An exemplary drive apparatus may include a first component and a moveable component, each configured to selectively grip the elongated member. In some examples, the first and moveable components may each include a gripping device. The moveable component may be configured to selectively move axially and rotationally with respect to a support surface to effect axial movement and rotation movement, respectively, of the elongated member with respect to the support surface within a range of motion of the moveable component. The moveable component may be configured to move the elongated member across a predetermined movement having a magnitude greater than the range of motion.

BRIEF DESCRIPTION OF THE DRAWINGS

While the claims are not limited to the illustrated embodiments, an appreciation of various aspects is best gained through a discussion of various examples thereof. Referring now to the drawings, illustrative embodiments are shown in detail. Although the drawings represent the embodiments, the drawings are not necessarily to scale and certain features may be exaggerated to better illustrate and explain an innovative aspect of an embodiment. Further, the embodiments described herein are not intended to be exhaustive or otherwise limiting or restricting to the precise form and configuration shown in the drawings and disclosed in the following detailed description. Exemplary embodiments of the present invention are described in detail by referring to the drawings as follows.

DETAILED DESCRIPTION

Figure 1:
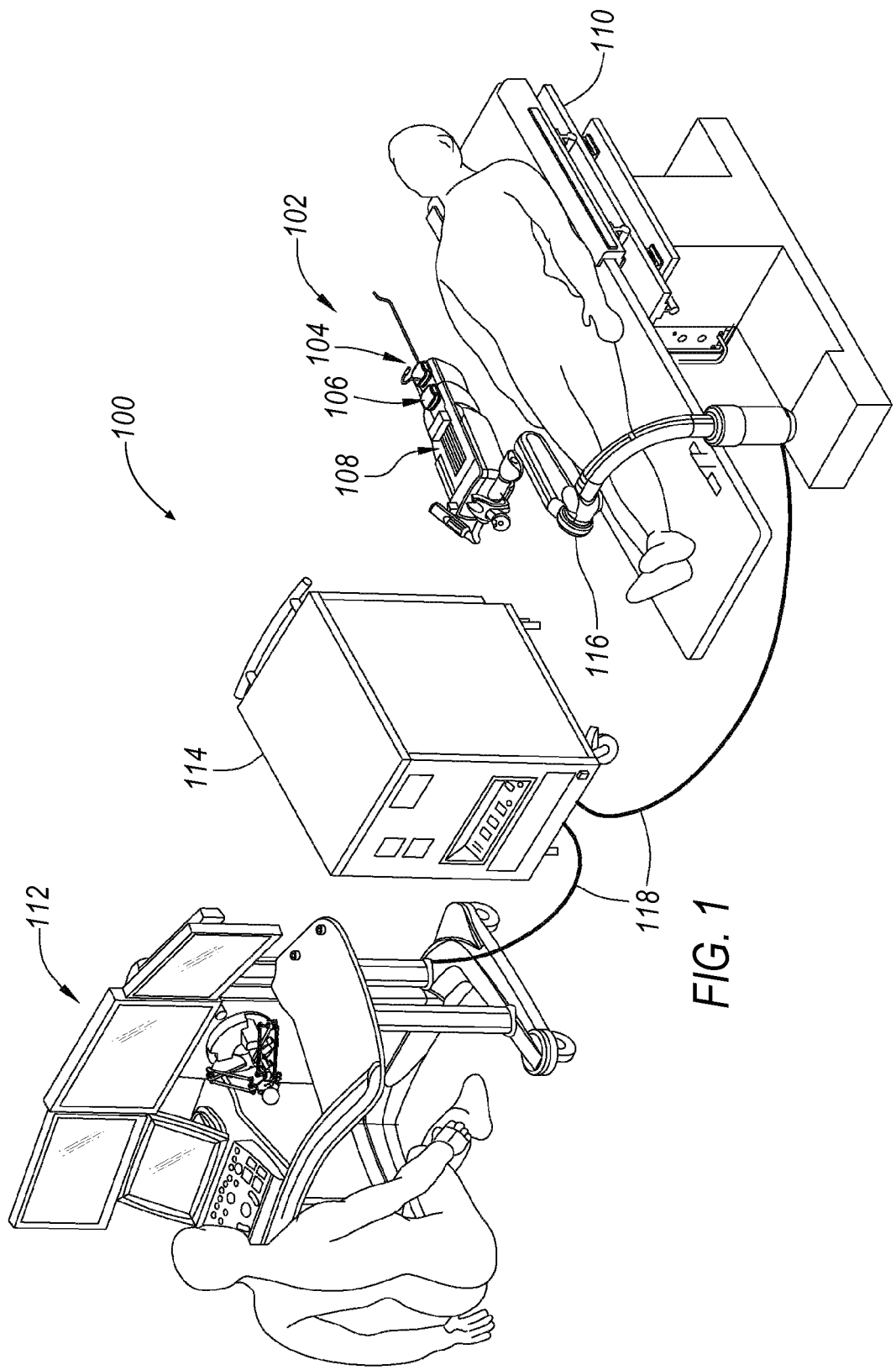
FIG. 1 is an illustration of a robotically controlled surgical system, according to one exemplary illustration.

Referring now to the drawings, illustrative embodiments are shown in detail. Although the drawings represent the embodiments, the drawings are not necessarily to scale and certain features may be exaggerated to better illustrate and explain an innovative aspect of an embodiment. Further, the embodiments described herein are not intended to be exhaustive or otherwise limit or restrict the invention to the precise form and configuration shown in the drawings and disclosed in the following detailed description.

Exemplary System and Drive Apparatuses

Referring to FIG. 1, a robotically controlled surgical system 100 is illustrated in which an apparatus, a system, and/or method may be implemented according to various exemplary illustrations. System 100 may include a robotic catheter assembly 102 having a robotic or first or outer steerable complement, otherwise referred to as a sheath instrument 104 (generally referred to as "sheath" or "sheath instrument") and/or a second or inner steerable component, otherwise referred to as a robotic catheter or guide or catheter instrument 106 (generally referred to as "catheter" or "catheter instrument"). Catheter assembly 102 is controllable using a robotic instrument driver 108 (generally referred to as "instrument driver"). During use, a patient is positioned on an operating table or surgical bed 110 (generally referred to as "operating table") to which robotic instrument driver 108 may be coupled or mounted. In the illustrated example, system 100 includes an operator workstation 112, an electronics rack 114 and associated bedside electronics box (not shown), a setup joint mounting brace 116, and instrument driver 108. A surgeon is seated at operator workstation 112 and can monitor the surgical procedure, patient vitals, and control one or more catheter devices. Operator workstation 112 may include a computer monitor to display a three dimensional object, such as a catheter instrument or component thereof, e.g., a guidewire, catheter sheath. Moreover, catheter instrument 502 may be displayed within or relative to a three dimensional space, such as a body cavity or organ, e.g., a chamber of a patient's heart. In one example, an operator uses a computer mouse to move a control point around the display to control the position of catheter instrument.

System components may be coupled together via a plurality of cables or other suitable connectors 118 to provide for data communication, or one or more components may be equipped with wireless communication components to reduce or eliminate cables 118. Communication between components may also be implemented over a network or over the internet. In this manner, a surgeon or other operator may control a surgical instrument while being located away from or remotely from radiation sources, thereby decreasing radiation exposure. Because of the option for wireless or networked operation, the surgeon may even be located remotely from the patient in a different room or building.

Figure 2:
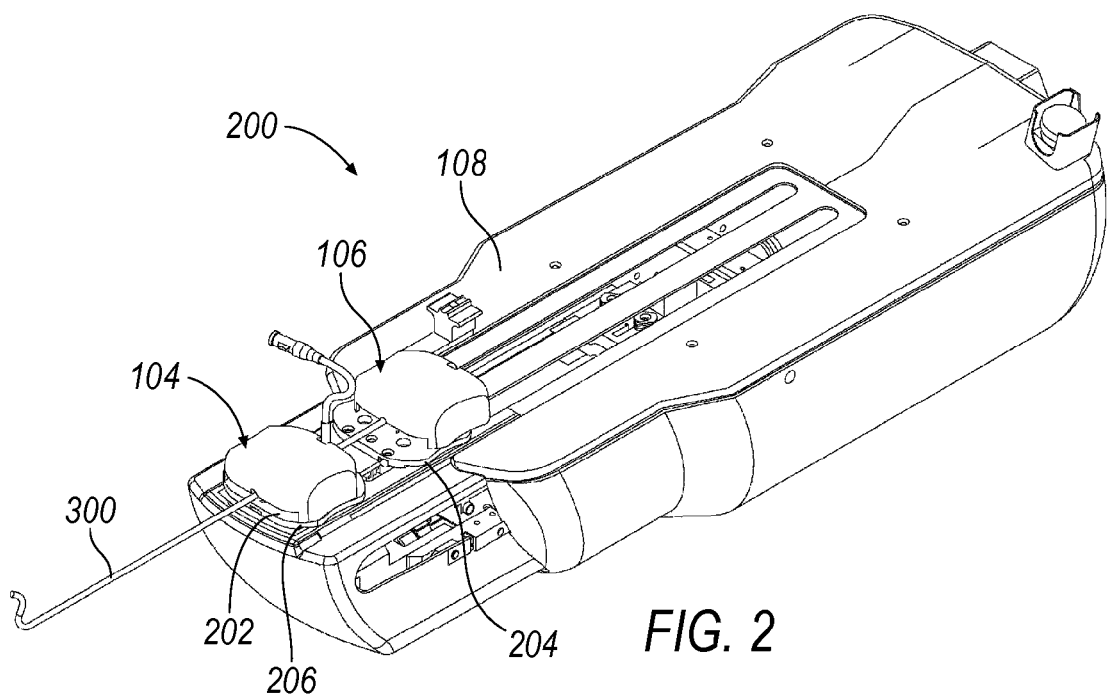
FIG. 2 is an illustration of an exemplary catheter assembly of the surgical system of FIG. 1.

Referring now to FIG. 2, an exemplary instrument assembly 200 is shown, including sheath instrument 104 and the associated guide or catheter instrument 106 mounted to mounting plates 202, 204 on a top portion of instrument driver 108. During use, catheter instrument 106 is inserted within a central lumen of sheath instrument 104 such that instruments 104, 106 are arranged in a coaxial manner. Although instruments 104, 106 are arranged coaxially, movement of each instrument 104, 106 can be controlled and manipulated independently. For this purpose, motors within instrument driver 108 are controlled such that carriages coupled to each of the instruments 104, 160 may allow the instruments 104, 106 to be driven forwards and backwards along the driver 108, e.g., with mounting plates securing the instruments to the driver 108 on bearings. As a result, a catheter 300 coupled to guide catheter instrument 106 and sheath instrument 104 can be controllably manipulated while inserted into the patient, as will be further illustrated. Additional instrument driver 108 motors (not shown in FIG. 2) may be activated to control bending of the catheter as well as the orientation of the distal tips thereof, including tools mounted at the distal tip. Sheath catheter instrument 106 is configured to move forward and backward for effecting an axial motion of the catheter, e.g., to insert and withdraw the catheter from a patient, respectively.

Figure 3:
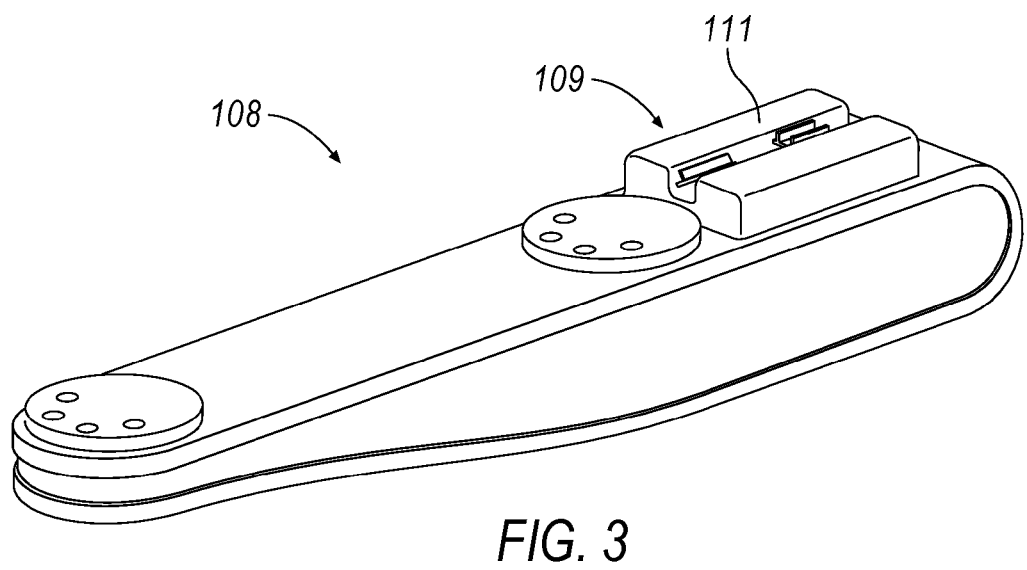
FIG. 3 is another exemplary illustration of an exemplary catheter assembly of the surgical system of FIG. 1.

Referring now to FIG. 3, another exemplary instrument 109 is illustrated mounted on the exemplary instrument driver 108. The instrument 109 includes a cover 111 and a drive apparatus, e.g., drive apparatus 400 or drive apparatus 1000, as will be described further below. During use the instrument 109 may be used to manipulate an elongate member included in the catheter assembly 102, e.g., a catheter guidewire (not shown in FIG. 3). Alternatively, the instrument 109 may be employed to manipulate a catheter sheath (not shown in FIG. 3). Although a single instrument 109 is illustrated in FIG. 3, in another exemplary illustration two instruments 109 may be employed in which a first instrument 109 is used to insert and roll a guidewire, which guidewire is inserted within a central lumen of a second instrument 109 (not shown in FIG. 3) such that the two instruments 109 are arranged in a coaxial manner, substantially as described above regarding the instruments 104, 106. Additionally, the instruments 109 may generally insert and rotate the associated elongate member, i.e., the guidewire and catheter sheath, independently, as described above regarding the instruments 104, 106. Accordingly, while the exemplary illustrations herein may generally focus on the insertion and rotation of a guidewire for a catheter, the instrument 109 may be used for insertion and rotation of any elongate member that is convenient.

Turning now to FIGS. 4-9, exemplary drive apparatus 400 is illustrated in further detail. As noted above, and as will be described further below, the drive apparatus 400 may generally include a moveable component 440. In the illustrated example, the moveable component 440 is a dynamic gripper 440. The drive apparatus may further comprise a first component 442. As illustrated in FIGS. 4-9, the first component 442 may be a static gripper 442, and in some exemplary approaches the static gripper 442 may be generally fixed with respect to the support surface 401. Each of the grippers 440, 442 may comprise a clamp 445, 447 having a pair of opposing pads 444a, 444b and 446a, 446b, respectively. Accordingly, the grippers 440, 442 may each selectively clamp an elongate member, e.g., a guidewire or catheter, between their respective opposing pads 444a, 444b and 446a, 446b.

The moveable component or dynamic gripper 440 may have a range of motion to which it is confined. For example, as will be described further below, the dynamic gripper 440 may be capable of axial movement in a direction A along a distance D. Additionally, the dynamic gripper 440 may be capable of limited rotational movement about an axis parallel to the direction of axial movement, e.g., to a range of plus or minus a predetermined angle with respect to a normal or center position. Nevertheless, the as described further below the dynamic gripper 440 may move an elongated component across a predetermined movement, e.g., an axial or rotational movement that may be provided by a user, that is greater than the axial or rotational range of motion.

Figure 5:
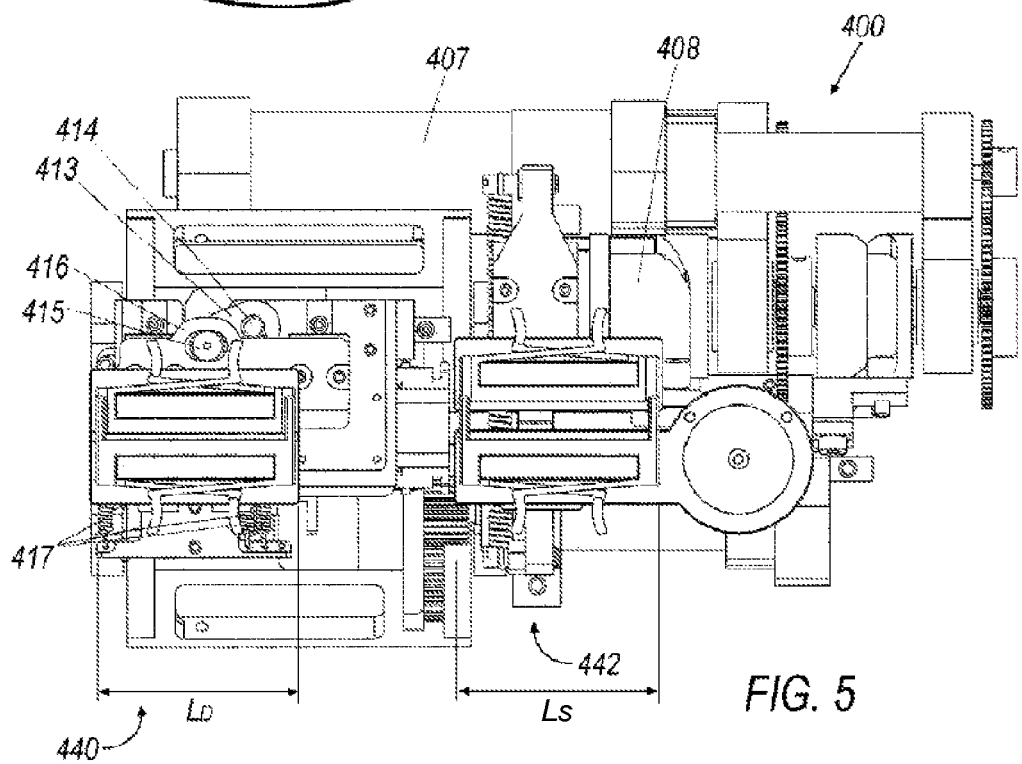
FIG. 5 is a top view of the exemplary drive apparatus of FIG. 4.
Figure 6:
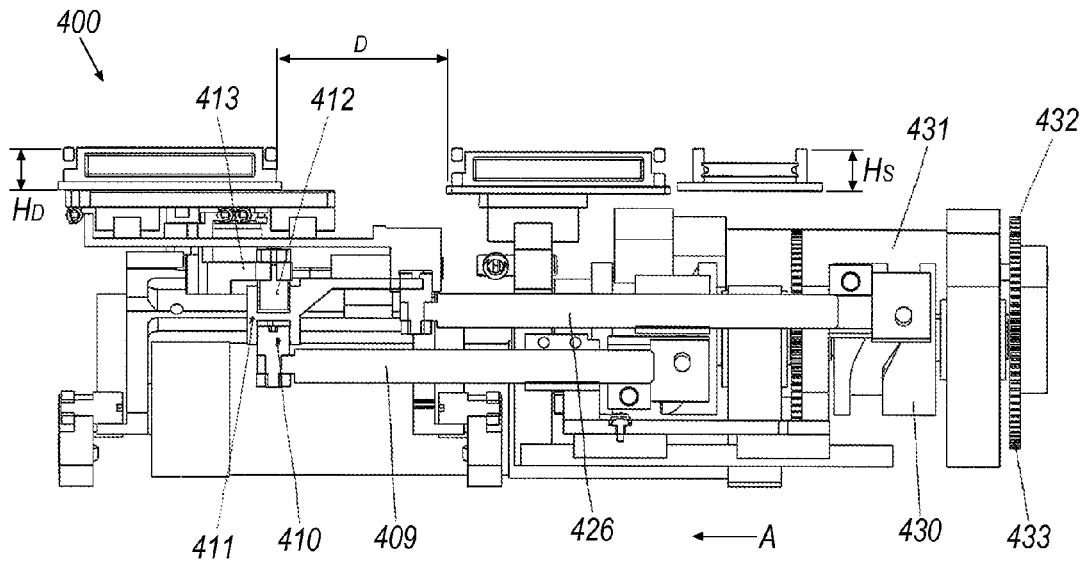
FIG. 6 is a side view of the exemplary drive apparatus of FIG. 4.

The pads 444 may each generally define a length $L_D$ in the axial direction associated with the elongate member, as best seen in FIG. 5. Similarly, the pads 446 may each generally define a length $L_S$ in the axial direction associated with the elongate member. As best seen in FIG. 6, the pads 444 may also each define a height $H_D$ in a direction perpendicular to the axial direction, i.e., in a direction corresponding to a direction of top loading the elongate member, as will be described further below. Moreover, the pads 446 may similarly each define a height $H_S$ in a direction perpendicular to the axial direction, i.e., in a direction corresponding to a direction of top loading the elongate member, as will be described further below.

An elongated member, e.g., a guidewire, may be wrapped about a slip detection wheel 406 that passively rotates in response to a length of the guidewire being moved by the dynamic grippers 440. The slip detection wheel 406 may be mounted on a rotatable member 405. Moreover, as will be described further below the wheel 406 may include optical marks allowing for tracking of the wheel 406 rotation, thereby allowing measurement of movement and/or slippage of the elongate member.

Figure 4:
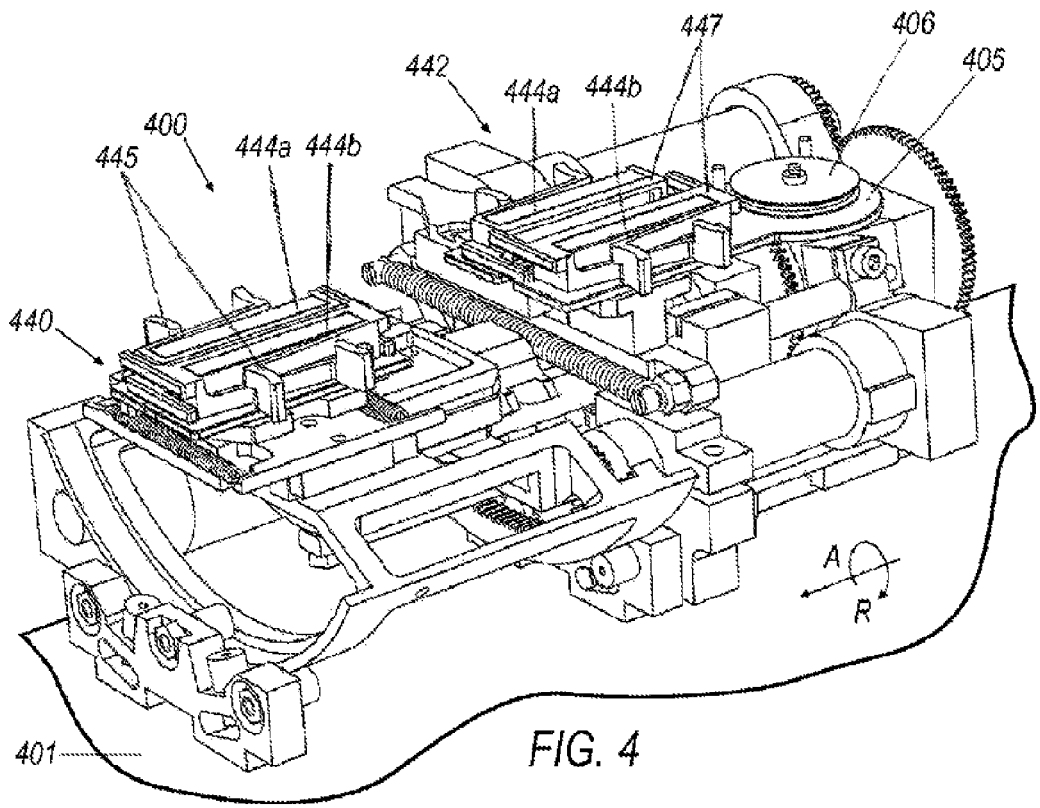
FIG. 4 is an illustration of an exemplary drive apparatus for an elongated member, e.g., a guidewire for a catheter.

As shown in FIG. 4, the grippers may each be mounted to a support structure 401, e.g., a top surface or support structure associated with the driver 108. The grippers 440, 432 are each configured to selectively grip an elongate member such as a catheter guidewire or sheath, merely as examples. Moreover, the dynamic gripper 440 is configured to generally move axially and rotationally with respect to the support structure 401 to effect a corresponding axial and rotational movement of the elongated member. By contrast, the static gripper 442 is generally not movable axially or rotationally with respect to the support structure 401. The static gripper 442 selectively closes and opens to grip and release the elongate member.

Generally, the static gripper 442 cooperates with the dynamic gripper 440 to effect axial movement (i.e., for insertion) along a direction A as illustrated in FIG. 4, and rotational movement R about the direction A of the elongate member. The grippers 440, 432 may generally work in sequence such that at least one of the grippers 440, 432 is gripping the elongate member at any given time. More specifically, during any movement of the guidewire, e.g., insertion, retraction, or rotational movement in either direction, the dynamic grippers 440 are closed, and static grippers 442 are open.

A range of axial motion associated with the dynamic grippers 440 may be finite, and in particular be limited to a predetermined axial distance D, as seen in FIG. 6. Accordingly, upon reaching a limit to the range of motion, i.e., at an axially furthest position in one direction, the dynamic grippers 440 generally release the elongate member, move back in an opposite direction, and re-grip the elongated member for continued axial movement. While the dynamic grippers 440 are not gripping the elongated member, the static grippers 442 may hold the elongated member in place to prevent movement or loss of position.

Axial and rotational motion of the elongated member may be governed by independent drive systems associated with the drive apparatus 400. For example, the dynamic gripper 440 may have separate motors or mechanisms controlling axial motion on the one hand and rotational motion on the other. Accordingly, insertion and rotation of the elongated member may be accomplished completely independently of the other. More specifically, the elongated member may be inserted axially while it is being rotated, or the elongated member may be inserted without any rotation. Moreover, the elongate member may be rotated without requiring any insertion motion at the same time.

Figure 8:
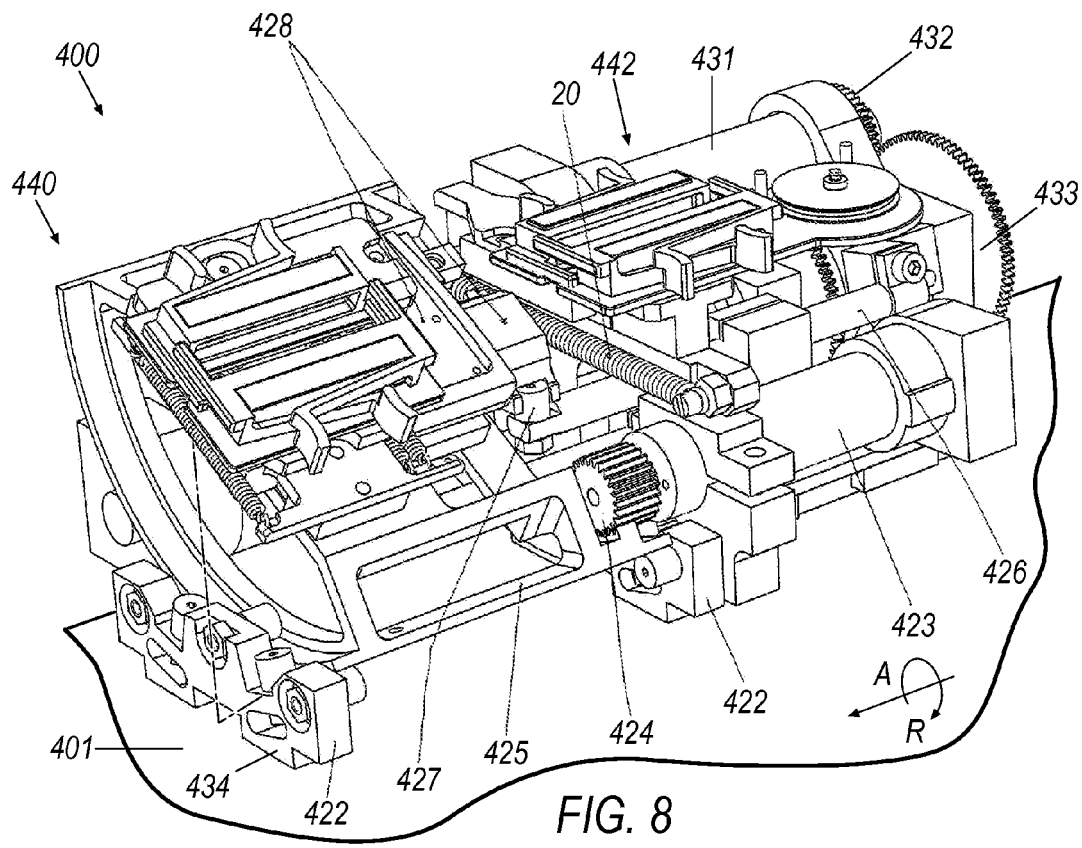
FIG. 8 is a perspective view of the exemplary drive apparatus of FIG. 4, with the dynamic gripper rotated to a maximum rotation in a clockwise direction.
Figure 9:
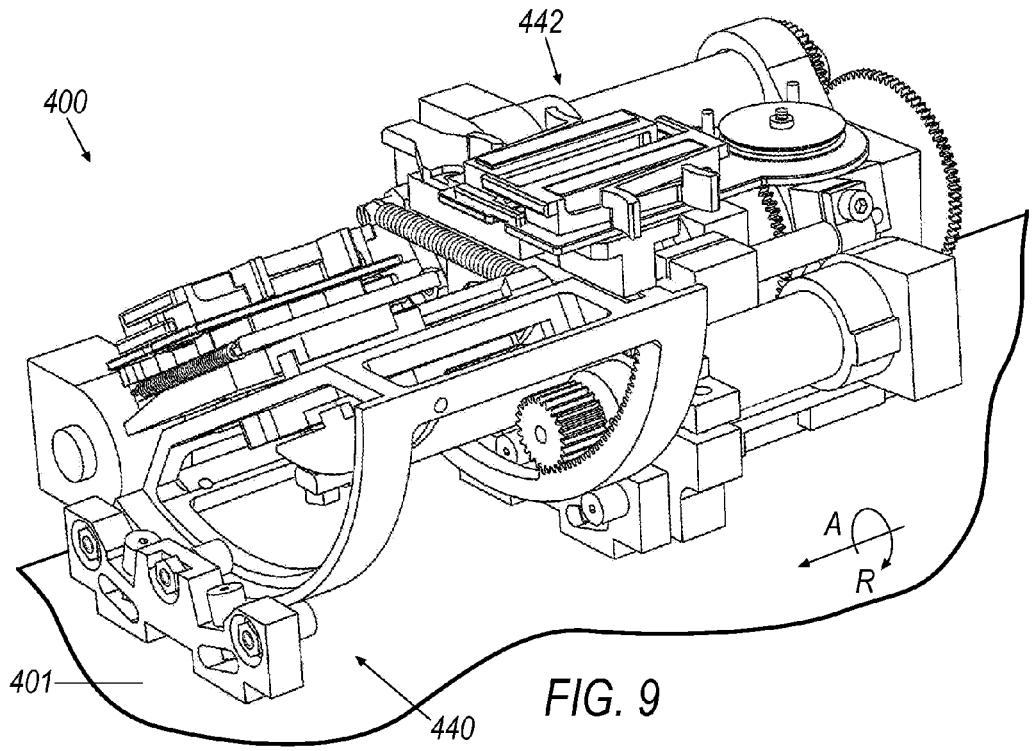
FIG. 9 is a perspective view of the exemplary drive apparatus of FIG. 4, with the dynamic gripper rotated to a maximum rotation in a counter-clockwise direction.

Turning now to FIGS. 8 and 9, rotational motion of the dynamic grippers 440 is described and shown in further detail. A rotation drive motor 423, as best seen in FIG. 8, may rotate a gear 424 engaging a carriage or swing platform 425 configured to rotate about an axis of rotation, e.g., in a rotational motion R about the direction of insertion A. The carriage 425 may be located by a pair of rolling posts 422 supported by a base structure 434. The base structure 434 may in turn be secured to the support structure 401. The carriage or swing platform 425 may be capable of rolling from a nominal or center position to any degree that is convenient. In one exemplary illustration, the carriage or swing platform 425 may be capable of rolling 30 degrees in either direction from a nominal or center position. More specifically, as illustrated in FIG. 8, swing platform 425 is rotated in a clock-wise direction thirty degrees away from a nominal or center position, i.e., as shown in FIG. 4. Moreover, as illustrated in FIG. 9, swing platform 425 is illustrated rotated in a counter-clockwise direction away from the nominal position.

Turning now to FIGS. 6 and 8, axial motion of the dynamic gripper 440 is illustrated in further detail. The dynamic gripper 440 may be axially moved by a shaft 426 which is linked to an axial drive motor 431 by way of cam 430, as best seen in FIG. 6. The cam 430 may be connected to the motor 431 via gears 432, 433. The opposite end of the shaft 426 may be connected to an axially movable platform 428 via a cam follower 427. Accordingly, the dynamic gripper 440 may be independently driven in an axial direction, e.g., for insertion, by the axial drive motor 431, and may be rotated independently by a rotation drive motor 423.

The static and dynamic grippers 442, 440 may each be configured to open to allow loading of an elongated member, e.g., a guidewire or catheter. Moreover, the grippers 440, 442 may generally allow "top loading" of the drive apparatus 400 in a direction perpendicular to the axial motion of the gripper 440. More specifically, the grippers 440, 442 may each generally open to allow the guidewire to be laid between the open grippers, e.g., from above the apparatus 400, without needing to "thread" the elongated member into the grippers 440, 442 axially. The ability to load the elongated member without requiring the catheter to be threaded through the drive apparatus 400 advantageously saves time, and also facilitates use of a sterile drape as will be described further below.

Figure 7:
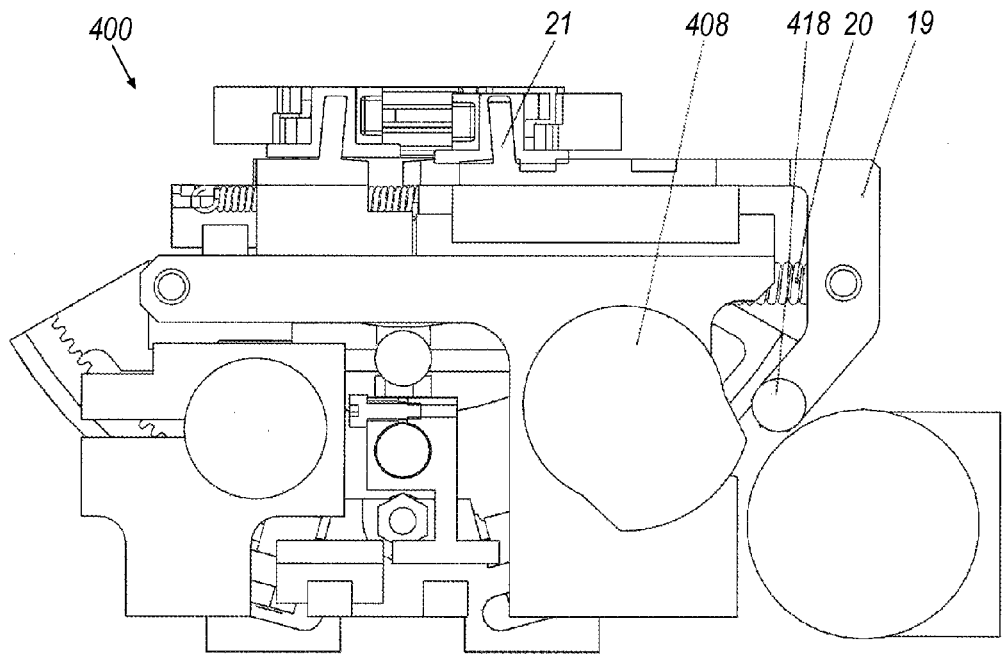
FIG. 7 is a rear view of the exemplary drive apparatus of FIG. 4.

Turning now to FIGS. 5-7, the opening and closing of the static gripper 442 and dynamic gripper 440 will now be explained in further detail. The dynamic gripper 440 may be opened by a grip open motor 407. For example, as best seen in FIGS. 5 and 6, a grip open motor 407 may be provided which drives a cam 408, which in turn actuates shaft 9. The shaft 9 has a cam follower 410 that provides axial motion to movable platform 411 and cam follower 412, which is attached to the lever 413 (see FIG. 6). The lever 13, as seen in FIG. 5, provides lateral motion through a rotation over shaft 414 to a dynamic gripper bracket 416 by way of cam follower 415. Cam 408 thus may generally provide only one way motion, to open the dynamic grippers 440. On the other hand, the dynamic grippers may be urged toward a closed position by a set of springs 417. For example, the springs 417 may act between the opposing pads included in the dynamic grippers 440, thereby urging the grippers 440 into a closed position absent a force applied by the grip open motor 407 to counteract the closing force of the springs 417.

As noted above, the static gripper 442 may be selectively opened and closed, independent of the opening and closing of the dynamic gripper 440. Nevertheless, the same cam 408 employed to open the dynamic grippers 440 may be used to selectively open the static grippers 442. For example, as best seen in FIG. 7, the cam 408 may include two separate profiles, with one configured to open the dynamic grippers 440, and another configured to open the static grippers 442. More specifically, the cam 408 as seen in FIG. 7 may be in proximity to a cam follower 418 that is connected to static gripper platform 419. The static gripper platform 419 may urge the opposing pads of the static grippers 442 apart. One or more compliant elements, e.g., spring 420, may generally urge the static gripper platform 419 toward a closed position where the static grippers 442 are clasped together, e.g., about a guidewire or catheter.

The platform 425 on which the dynamic grippers 440 are mounted may generally move in relation to the support surface 401, as noted above. The platform 425 thus may also be moving in relation to the cam follower 410, shaft 409, and cam 408 used to effect opening and closing movement of the dynamic grippers 440. Accordingly, the movement of the shaft 409 is in relation to the moving platform 425, and thus the opening movement of the cam 408 may need to account for this additional relative movement in order to open the dynamic grippers 440.

As briefly described above, the grippers 440, 442 generally allow a top loading of the elongated member, e.g., a guidewire, thereby increasing the speed with which the guidewire may be loaded into the drive apparatus 400. Additionally, the positioning of the grippers 440, 442 and the opposing pads 444, 446 may also facilitate the use of a sterile drape that generally maximizes the potential for reusing components of the drive apparatus 400. In other words, the sterile drape may allow for keeping nearly the entire drive apparatus 400 out of the sterile environment, defining in part a disposable portion of the system 100 that is within the sterile environment.

Turning now to FIGS. 10-14, another exemplary drive apparatus 1000 is illustrated in further detail. The drive apparatus 1000 may generally include a moveable component such as a dynamic gripper 1050. The drive apparatus may further comprise a fixed component. In the example illustrated in FIGS. 10-14, the fixed component includes at least one static gripper. As illustrated in FIGS. 10-14 the fixed component includes two static grippers 1052a, 1052b. More specifically, the fixed component includes a first static gripper 1052a, and a second static gripper 1052b. The dynamic gripper 1050 may comprise a pair of opposing pads 1003, 1004. Similarly, a first one of the static grippers 1052a may comprise a pair of opposing pads 1005a, 1006a, and the other static gripper 1052b may also comprise a pair of opposing pads 1005b, 1006b. Accordingly, the grippers 1050, 1052a, and 1052b may each selectively clamp an elongate member, e.g., a guidewire or catheter, between their respective opposing pads 1003/1004, 1005a/1006a, and 1005b/1006b. The pads 1003/1004, 1005a/1006a, and 1005b/1006b may each be relatively soft with respect to the particular elongate member being employed, in order to more securely grip the elongate member and minimize potential damage to the elongate member, e.g., by spreading grip load across an increased surface area of the elongate member.

Figure 12:
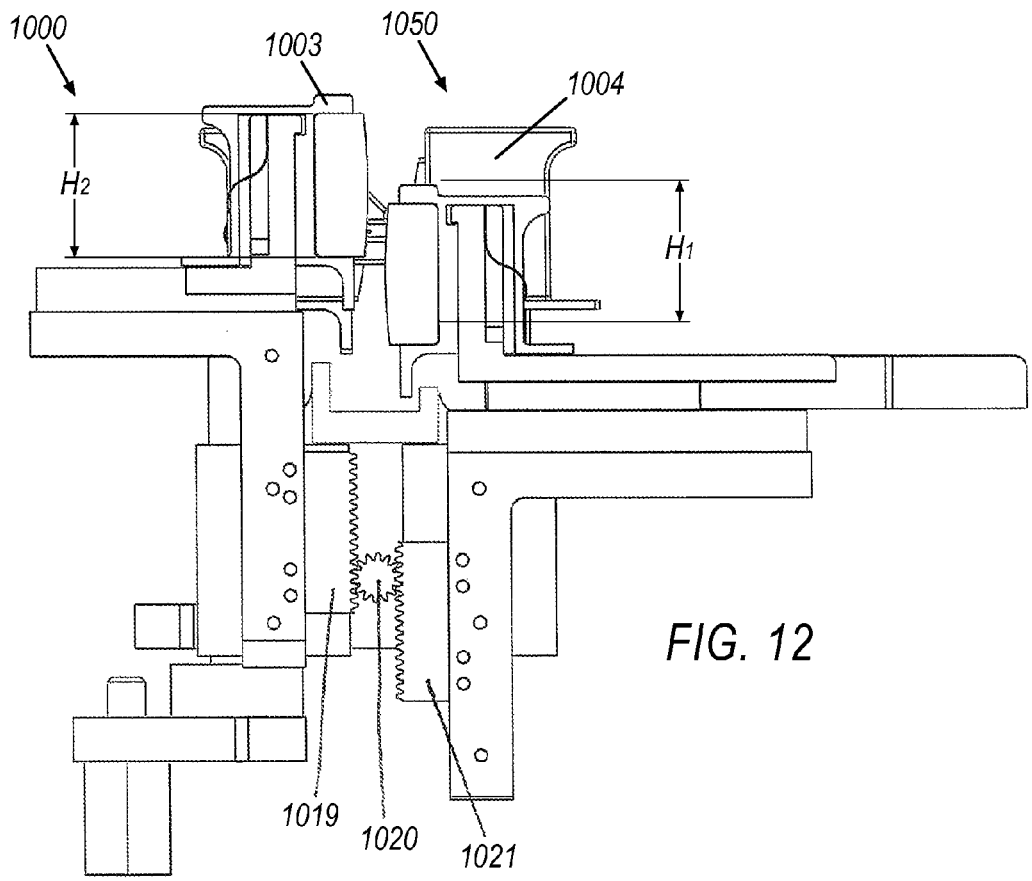
FIG. 12 is a front view of the exemplary drive apparatus of FIG. 10.
Figure 13:
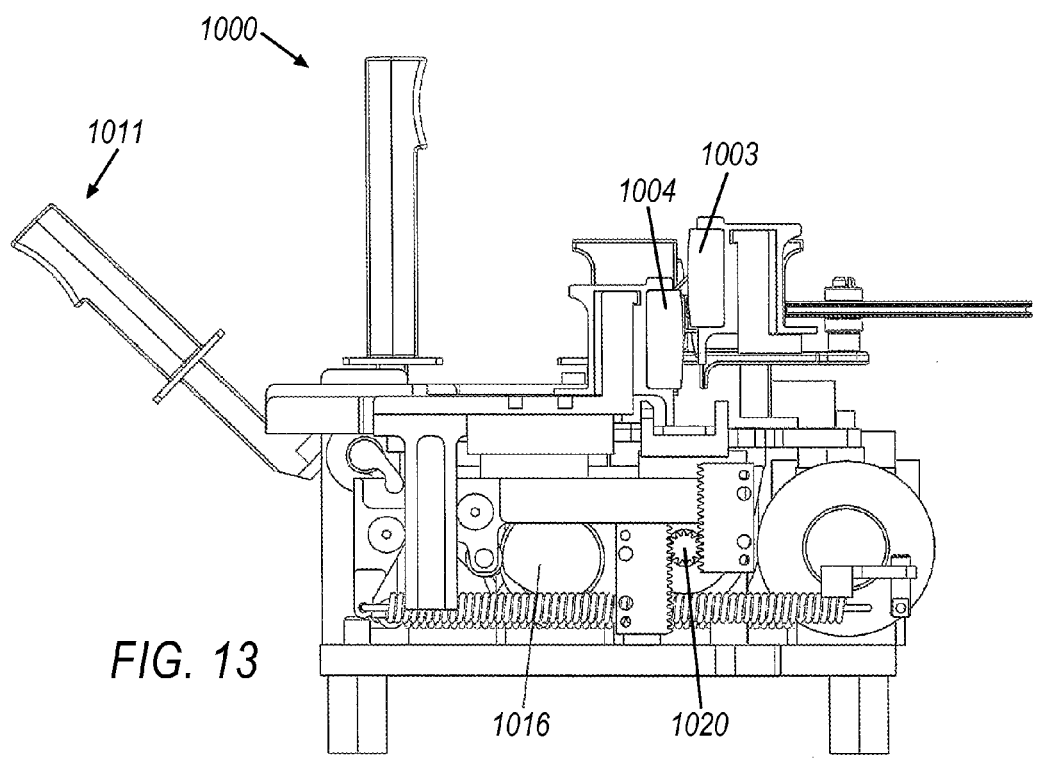
FIG. 13 is a rear view of the exemplary drive apparatus of FIG. 10.

As best seen in FIGS. 12 and 13, the pads 1003, 1004 of the dynamic gripper 1050 each define generally arcuate profiles for engaging the elongate member (not shown in FIGS. 12 and 13). More specifically, the pads 1003, 1004 each have curved pad surfaces 1098, 1099, respectively. Accordingly, the pads 1003, 1004 may engage an elongate member along a longitudinal line extending parallel to the elongate member, i.e., axially with respect to the dynamic gripper 1050. In other exemplary approaches, the surfaces of the pads 1003, 1004 may be generally flat. The pads 1005a/1006a and 1005b/1006b of the static grippers 1052a, 1052b, respectively, may similarly define either curved or flat engagement surfaces for engaging an elongate member.

Figure 19:
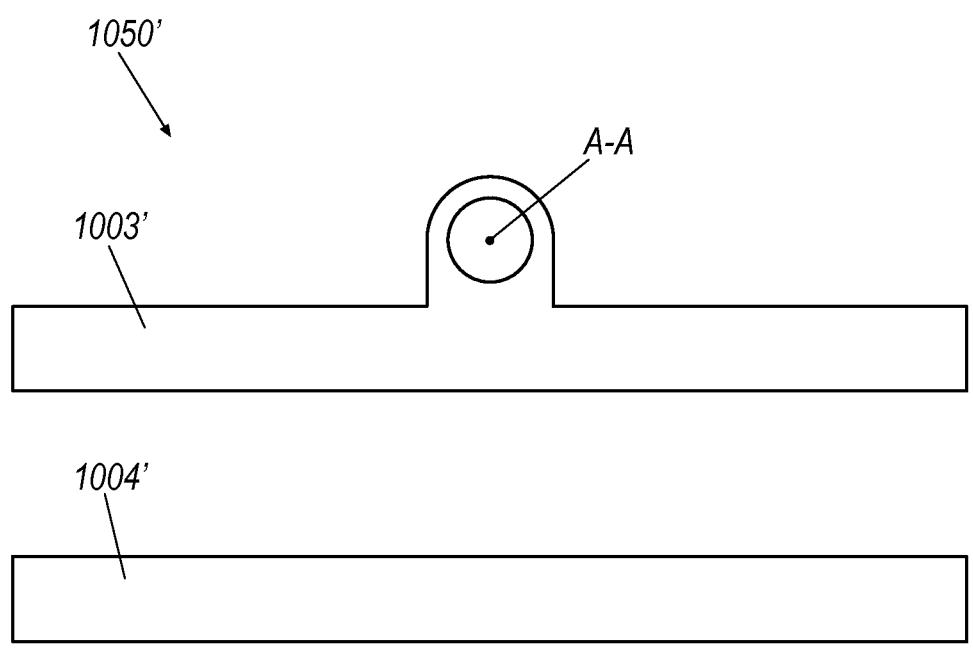
FIG. 19 is a top view of an exemplary pivotable pad for a gripper.

Turning now to FIG. 19, in another exemplary approach one of the pads 1003' of a dynamic gripper 1050' may be pivotable about a substantially vertical axis A-A with respect to an opposing pad 1004'. While the pads 1003/1004, 1005a/1006a, and 1005b/1006b described in regard to FIGS. 10-14 are illustrated as being generally fixed rotationally with respect to one another, a pivotable pad 1003' may be employed in place of any of the rotationally fixed pads. The pivotable pad 1003' may generally improve grip of an elongate member by minimizing any loss of grip due to misalignment of the pad 1003' or 1004'. More specifically, to any extent the pad 1004' is possibly misaligned, the pad 1003' will generally automatically rotate about the vertical axis A-A as the associated gripper, e.g., dynamic gripper 1050, closes upon the elongate member. The pivoting pad 1003' may thereby ensure a substantially parallel alignment of the two pads 1003', 1004' as the gripper 1050' closes upon the elongate member. Moreover, the pivotable pad concept may be applied not only to a dynamic gripper 1050', but also to a static gripper, e.g., static grippers 1052a, 1052b.

Similar to the drive apparatus 400, the moveable component or dynamic gripper 1050 of the drive apparatus 1000 may have a predetermined range of motion which it is confined to. For example, as will be described further below, the dynamic gripper 1050 may be capable of axial movement in a direction A along a predetermined distance $D_2$ (see FIG. 10). Additionally, the dynamic gripper 1050 may be capable of imparting a limited rotational movement to the elongate member about an axis parallel to the direction of axial movement, e.g., to a range of plus or minus a predetermined angle with respect to a normal position. More specifically, as will be described further below the pads 1003, 1004 of the dynamic gripper 1050 may generally translate vertically with respect to one another across a limited range of translational motion, e.g., as defined by a gear and rack system. Nevertheless, the dynamic gripper 1050 may move an elongated component across a movement, e.g., an axial or rotational movement, for example as commanded by a user or surgeon, that is greater than the predetermined axial or rotational motion capable of the dynamic gripper 1050 in a single vertical stroke of the dynamic grippers 1050.

Figure 14:
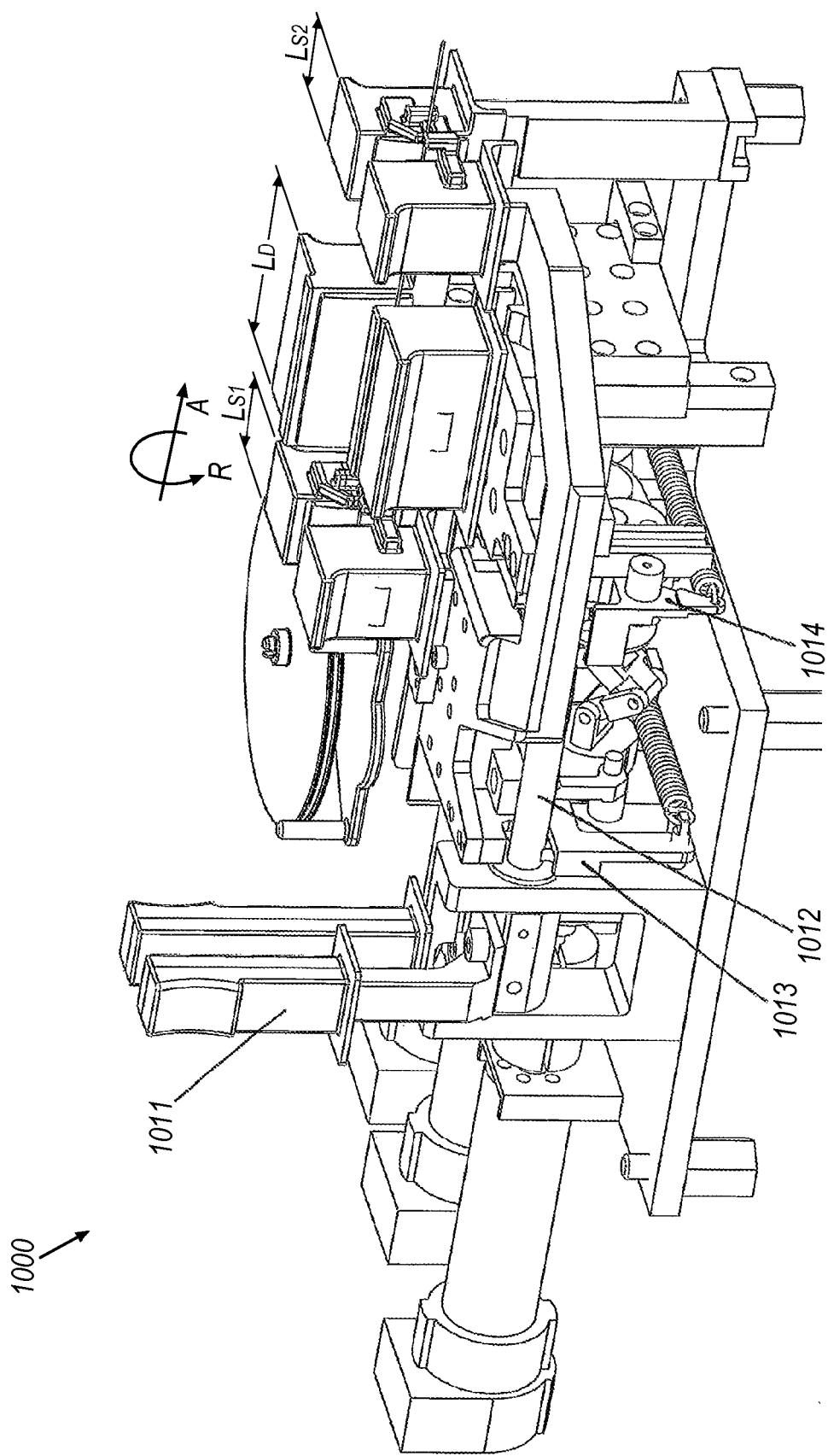
FIG. 14 is another perspective view of the exemplary drive apparatus of FIG. 10, with the grippers placed in an open position.

The pads 1003, 1004 of the dynamic gripper 1050 may generally define a length $L_D$ in the axial direction associated with the elongate member, as best seen in FIG. 14. Similarly, the pads 1005a, 1006a and 1005b, 1006b of the first and second static grippers 1052a, 1052b, respectively, may generally define respective lengths $L_{S1}$, $L_{S2}$ in the axial direction associated with the elongate member. Similar to the heights $H_D$ and $H_S$ described above regarding drive apparatus 400, the pads 1003/1004, 1005a/1006a, and 1005b/1006b may each generally define an axial height, i.e., in a direction perpendicular to the direction of axial insertion A and corresponding to a direction from which an elongated member may be placed in between the pads. For example, as best seen in FIG. 12, the pads 1003, 1004 of the dynamic grippers 1050 may define respective axial heights $H_2$ and $H_1$, which may be equal. The pads 1003/1004, 1005a/1006a, and 1005b/1006b may each generally be open to a space above the pads when opened, e.g., as shown in regard to the dynamic pads 1003, 1004 in FIG. 12, allowing an elongated member extending across the pads axially to be laid in between the pads 1003/1004, 1005a/1006a, and 1005b/1006b.

An elongated member, e.g., a guidewire, may be wrapped about slip detection wheel 1002 that passively rotates in response to a length of the guidewire being moved by the dynamic grippers 1050. The slip detection wheel 1002 may be mounted on a support 1001. Moreover, as will be described further below the wheel 1002 may include optical marks allowing for tracking of the wheel 1002 rotation, thereby allowing measurement of movement of the elongate member. It should be noted that for stiffer elongate members, it may not be necessary to wrap the elongate member about the slip detection wheel. Instead, the wheel may be configured to just contact the elongate member and rotation is imparted to the passive wheel via friction between the wheel and the surface of the elongate member.

Figure 10:
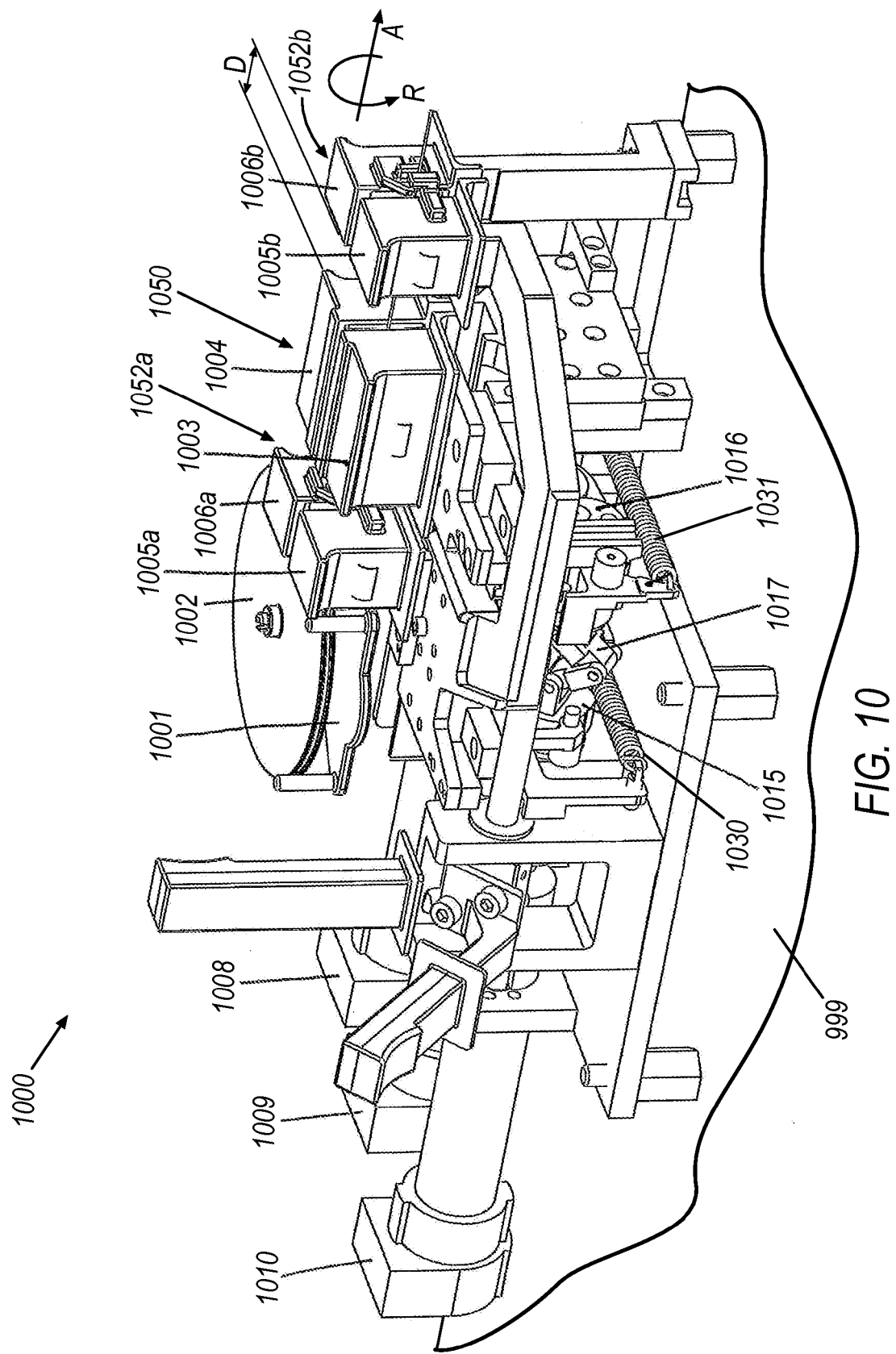
FIG. 10 is an illustration of another exemplary drive apparatus for an elongated member, e.g., a guidewire for a catheter.

As shown in FIG. 10, the static grippers 1052a, 1052b and dynamic gripper 1050 may each be mounted to a support structure 999, e.g., a top surface or support structure associated with the driver 108. The grippers 1050, 1052 are may each be configured to selectively grip an elongate member such as a catheter guidewire or sheath, merely as examples. Moreover, the dynamic gripper 1050 is configured to generally move axially with respect to the support structure 999 to effect a corresponding axial movement of the elongated member. The pads 1003, 1004 of the dynamic gripper 1050 are also configured to translate in a vertical direction across a fixed range of motion to impart rotational motion to the elongate member with respect to the support structure 999. By contrast, the static grippers 1052a and 1052b are generally not movable axially or rotationally with respect to the support structure 401. The static grippers 1052a and 1052b selectively close and open to grip and release the elongate member.

Generally, similar to the drive apparatus 400 described above, the static grippers 1052a and 1052b of the drive apparatus 1000 each cooperate with the dynamic gripper 1050 to effect axial movement (i.e., for insertion or retraction) along a direction A as illustrated in FIG. 10, and rotational movement R about the direction A of the elongate member. The static grippers 1052a, 1052b may generally work in sequence with the dynamic grippers 1050 such that at least one of the grippers 1050, 1052a, and 1052b is gripping the elongate member at any given time. More specifically, during any movement of the guidewire, e.g., insertion, retraction, or rotational movement in either direction, the dynamic grippers 1050 are closed, and the static grippers 1052a and 1052b are open. Moreover, the static grippers 1052a, 1052b may generally work in concert, such that the static grippers 1052a, 1052b are either both open or both closed together.

A range of axial motion associated with the dynamic grippers 1050 may be finite, and in particular be limited to a predetermined axial distance $D_2$, as seen in FIG. 10. In the illustrated example having two static grippers 1052a, 1052b, a range of motion of the dynamic gripper 1050 may be limited by the static gripper 1052a on one end and the other static gripper 1052b on the other end. However, as noted above, in other exemplary approaches only one static gripper 1052 may be present, and thus the axial motion of the dynamic gripper 1050 may be limited by other factors. Nevertheless, the dynamic gripper 1050 may have some predetermined range of axial motion. Accordingly, upon reaching a limit to the range of motion, i.e., at an axially furthest position in one direction, the dynamic grippers 1050 generally release the elongate member, move back in an opposite direction, and re-grip the elongated member for continued axial movement. While the dynamic grippers 1050 are not gripping the elongated member, the static grippers 1052a and/or 1052b may hold the elongated member in place to prevent movement of the elongated member or loss of position.

Axial and rotational motion of the elongated member may be governed by independent drive systems associated with the drive apparatus 1000, as with drive apparatus 400. For example, the dynamic gripper 1050 may have separate motors or mechanisms controlling axial motion on the one hand and rotational motion on the other. Accordingly, insertion and rotation of the elongated member may be accomplished completely independently of the other. More specifically, the elongated member may be inserted axially while it is being rotated, or the elongated member may be inserted without any rotation. Moreover, the elongate member may be rotated without requiring any insertion motion at the same time.

Referring now to FIGS. 10, 13, and 14, opening and closing of the grippers is described and shown in further detail. The drive apparatus 1000 may be generally closed initially. In order to open the grippers, lever 1011 may be manually moved to a vertical position, e.g., as illustrated in FIG. 14. The movement of the lever 1011 may rotate a shaft 1012 that is configured to move a static pad bracket 1013 which in turn opens the static pads 1005a and 1005b with respect to their corresponding static pads 1006a and 1006b, respectively. A dynamic pad bracket 1014 may open the dynamic pads 1003, 1004 of the dynamic gripper 1050 in a similar manner. In one exemplary illustration, cams may be positioned on the shaft 1012 for urging the brackets 1013, 1014 in a direction opening the pads of each of the static grippers 1052a, 1052b and the dynamic grippers 1050, respectively. Moreover, the pads of the static grippers 1052a, 1052b and the dynamic grippers 1050 may be opened in sequence, i.e., separately from one another. For example, as best seen in FIGS. 10, 13, and 14, cams 1015 and 1016 may be connected by a coupling 1017 that is driven by motor 1010. The cams 1015, 1016 may act upon the static pad bracket 1013 and dynamic pad bracket 1014, respectively, thereby opening each. The static pad bracket 1013 may be urged into a closing position by a spring 1030, while the dynamic pad bracket 1014 may be urged into a closing position by a spring 1031. Accordingly, the static pad bracket 1013 and dynamic pad bracket 1014 generally may remain closed in the absence of a force applied to the brackets 1013, 1014 tending to open either of the brackets 1013, 1014.

Figure 11:
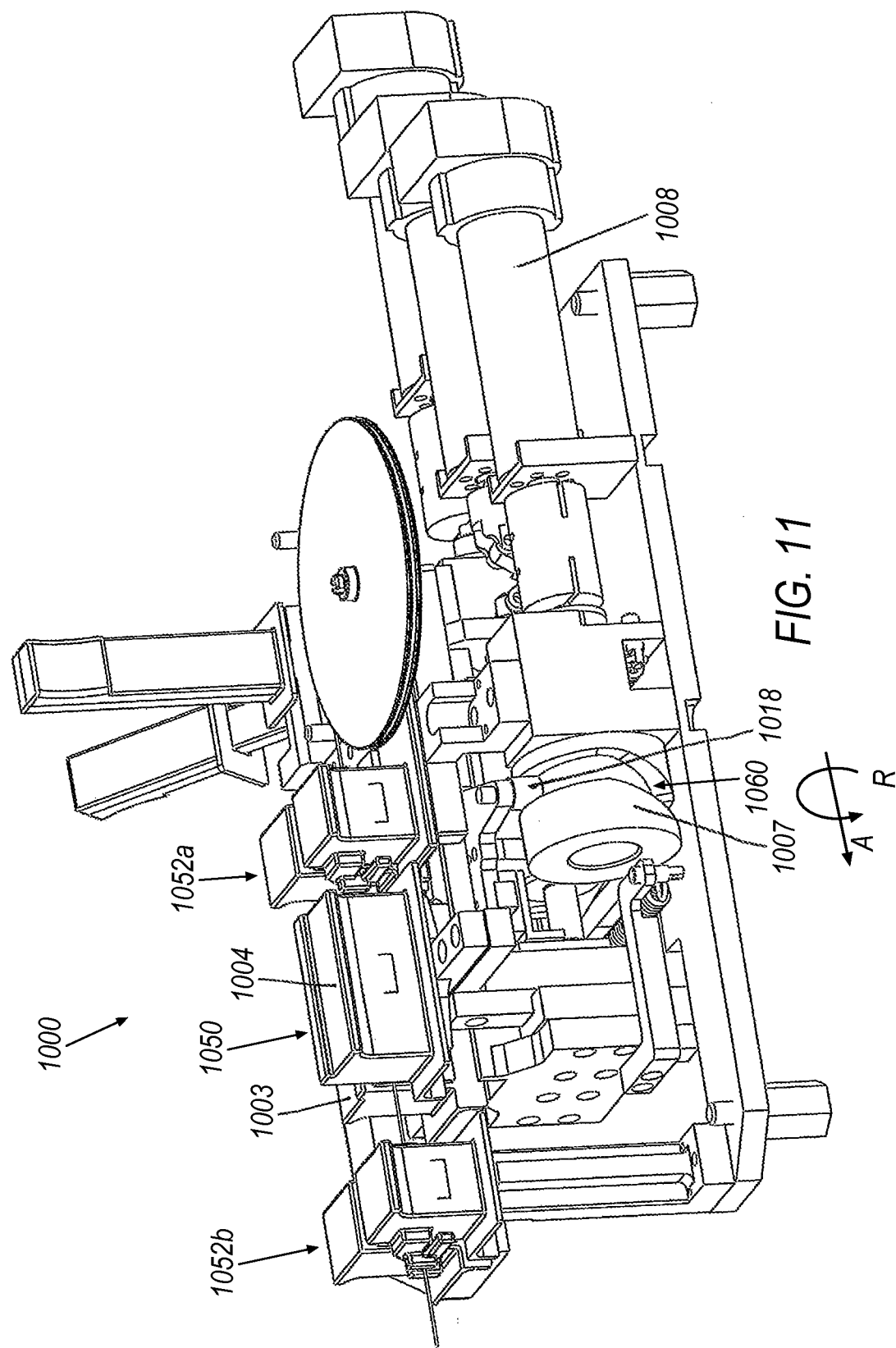
FIG. 11 is another perspective view of the exemplary drive apparatus of FIG. 10.

Turning now to FIGS. 10, 11, and 12, axial motion of the drive apparatus 1000, e.g., for insertion or retraction of an elongate member, is described in further detail. Axial movement of the dynamic gripper 1050, i.e., to effect an insertion or refraction motion of the dynamic gripper 1050, may be driven by a cam 1007 that is turned by motor 1008, as best seen in FIG. 11. More specifically, cam follower 1018 may follow the cam, e.g., within a groove 1060 defined by the cam 1007, thereby imparting axial motion to dynamic gripper 1050, including both of the opposing pads 1003, 1004.

Turning now to FIGS. 10 and 12 a mechanism for imparting a rotational motion to an elongate member using the drive apparatus 1000 is described in further detail. As best seen in FIG. 12, which is a cross section of the apparatus 1000, a gear shaft 1020 may be connected through a coupling to a dedicated motor 1009 (see FIG. 10). The gear shaft 1020 may provide relative vertical motion to a first gear rack 1019 that is opposed by a second gear rack 1021. The relative vertical motion is transferred to the dynamic gripper 1050. More specifically, a first one of the pads 1003 of the dynamic gripper 1050 translates upward and downward with the first gear rack 1019, while the other pad 1004 translates upward and downward with the second gear rack 1021. Accordingly, the relative vertical movement between the pads 1003, 1004 imparts a rolling motion to an elongate member held between the pads 1003, 1004.

Pads 1003 and 1004 may be designed to optimize the gripping and rolling performance of the elongate member. For example, in one exemplary illustration, a high durometer material that does not engulf the elongate member is used, which may generally prevent pads 1003 and 1004 from contacting each other. This ensures that the spring force closing the grippers is substantially entirely applied to the elongate member and is not transferred from one gripper to the other, ensuring reliable grip on the elongate member. In another exemplary illustration, the contact surface of the pads 1003 and 1004 is beveled in a convex shape such that there is less chance that the pads will contact each other due to any misalignment or non parallelism in the gripper mechanism.

Initially, the pads 1003, 1004 of the dynamic grippers 1050 and the pads 1005a, 1006a, 1005b, 1006b of the static grippers 1052a, 1052b may be manually opened with the lever 1011, as best seen in FIG. 10. An elongate member, e.g., a guidewire, may be top loaded into the apparatus 1000. More specifically, a guidewire may be loaded around wheel 1002 and laid in between the pads 1005a and 1006a of the first static gripper 1052a, the pads 1003 and 1004 of the dynamic gripper 1050, and the pads 1005 band 1006b of the second static gripper 1052b. More specifically, the elongate member may generally be laid between the pads 1003/1004, 1005a/1006a, and 1005b/1006b from above, allowing the elongate member to be extended and laid in between the pads instead of requiring that the elongate member be threaded axially through the pads. During axial motion, e.g., insertion or retraction, an elongate member such as a guide wire or catheter will be pulled off of or pushed onto wheel 1002, which may passively rotate according to the insertion motion driven by the dynamic gripper 1050 with respect to a wheel support 1001 of the drive apparatus 1000. As noted above, rotation of the wheel 1002 may be monitored, e.g., by an optical sensor, to allow for measurement of any axial movement of the elongate member. During axial movement of the elongate member, e.g., insertion or retraction, and also during rotational movement, the dynamic pads 1003 and 1004 are generally closed, thereby trapping the elongate member therebetween as a result of a grip imparted to the elongate member or guidewire. Additionally, during axial or rotational motion of the elongate member, the pads 1005a, 1006a of the first static gripper 1052a and the pads 1005b, 1006b of the second static gripper 1052b remain open, thereby generally freely allowing relative movement of the elongate member with respect to the static grippers 1052a, 1052b. Upon reaching a limit of rotational or axial motion, the pads 1005a, 1006a of the first static gripper 1052a and the pads 1005b, 1006b of the second static gripper 1052b may be closed. The pads 1003 and 1004 of the dynamic gripper 1050 may then be opened, and moved within its range of motion (i.e., along distance D) to allow regripping of the elongated member, while the static grippers 1052a, 1052b maintain the axial and rotational position of the elongated member. The cycle may then be repeated to allow further axial and/or rotational movement of the elongated member.

Figure 15:
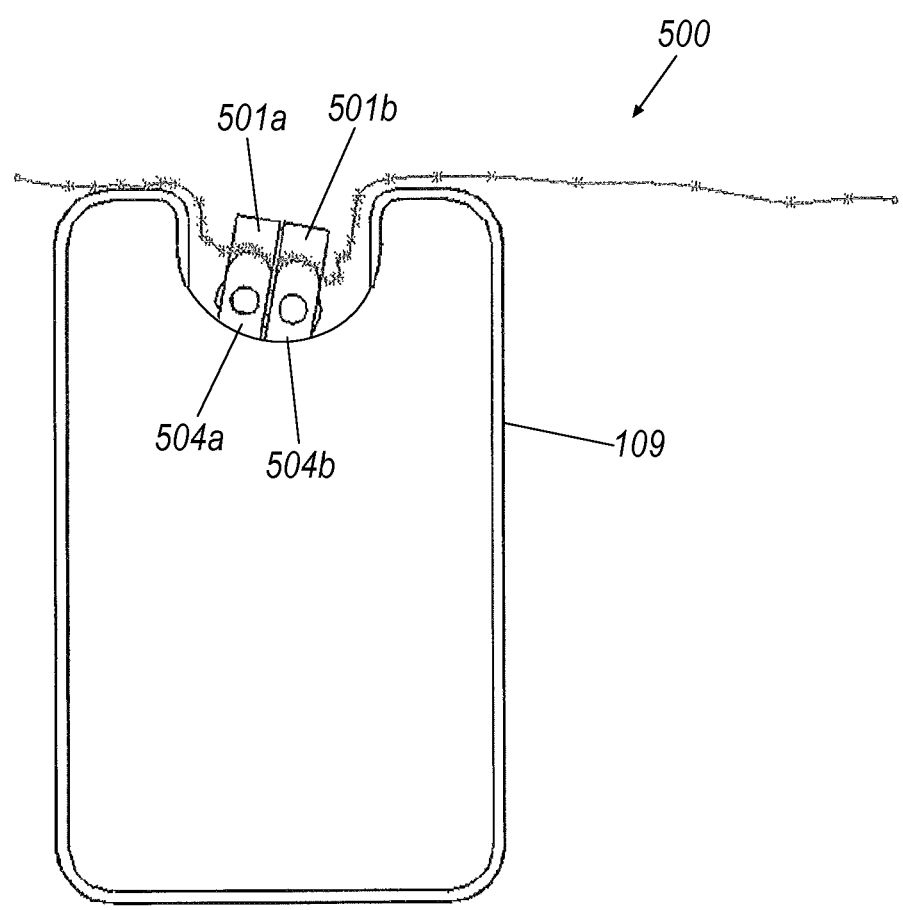
FIG. 15 is a front view of an exemplary instrument with a sterile drape assembly.

Turning now to FIG. 15, an exemplary sterile drape assembly is illustrated. An exemplary drape assembly may include a sterile drape 500 generally positioned over the instrument 109. The sterile environment may thereby be confined to the area above the drape 500, allowing use and reuse of the instrument 109 and essentially all components thereof that are positioned beneath the drape. The drape 500 may be positioned over a set of grippers 504a, 504b using associated caps 501a, 501b. For purposes of the illustration shown in FIG. 15, the grippers 504a, 504b may correspond to any of the static grippers 1052a, 1052b or dynamic grippers 1050 of the apparatus 1000, or the static gripper 442 or dynamic gripper 440 of the apparatus 400. For example, the caps 501 may be molded into the drape 500, and may be fitted to the grippers 504, thereby securing the drape 500 in place over the grippers 504. Moreover, the caps 501 may generally allow for gripping of an elongated member, e.g., a guidewire or catheter, using the caps 501, thereby allowing the elongated member to be in the sterile environment. The drape 500 and caps 501 may be included in a disposable portion of the system 100, i.e., which must be disposed of after a procedure, while substantially all components of the system 100, and in particular the drive apparatus 400 or drive apparatus 1000, is kept out of the sterile environment and therefore may be reused.

It should be understood that the designs presented here are merely exemplary. For example, while apparatus 400 and apparatus 1000 are both described as having one set of fixed grippers and one set of dynamic grippers, alternative approaches may have two pairs of dynamic grippers instead of one static pair and one dynamic pair. The second pair of dynamic grippers may perform similar duties as the static grippers described herein with respect to the first set of dynamic grippers (i.e., hold the elongate member while the first dynamic gripper is returning). Moreover, the second dynamic gripper may also apply axial and rotation movement just like the first dynamic gripper.

It should also be understood that the stroke length and gripper length shown for apparatuses 400 and 1000 are also merely exemplary. For example, the distance between the grippers which is approximately equal to the stroke length is shown to be approximately the same length as each of the grippers. This may not be true in all cases. For example, for stiffer elongate members that have greater buckling strength, there may be a significantly longer length between the grippers, or effectively a significantly longer stroke. In addition, if the elongate member that is being manipulated has a high friction surface, then shorter grippers may be appropriate. Also, the length of the static and dynamic grippers are shown to be equal. It is likely that the static gripper length may be shorter than the dynamic gripper since the static gripper just needs to hold the device.

The rotational mechanism of apparatus 400 is shown to have approximately 60° of rotation in both directions. Again, this is merely an exemplary illustration. the 60 degrees of rotation may generally permit a doctor to intervene manually and remove the robotic system if the robotic system is stopped at any point during a procedure, and the guidewire will always be presentable towards the top of the mechanism for removal. If for example, there was 180° of rotational movement on this mechanism, there may be times when the grippers are inverted making it difficult to remove the guidewire. In addition, large rotational strokes make it more difficult to manage the sterile barrier because it may lead to more winding up of the drape. Nevertheless, any angle of rotation may be employed that is convenient.

It should also be noted that even though most of the descriptions used here describe the elongate member as a guidewire, it may also be a catheter, a sheath, a microcatheter, a therapeutic device such as a stent or balloon or artherectomy device for example.

Control of Discontinuous/Finite Drive Apparatus to Provide Continuous/Infinite Movement As noted above, the dynamic gripper 440 of the apparatus 400 and the dynamic gripper 1050 of the apparatus 1000 generally may have a finite range of motion in the axial direction, i.e., a range of motion across an axial distance D as best seen in FIGS. 6 and 10, respectively. Additionally, the dynamic grippers 440 and 1050 have a finite range of rotational motion, i.e., a maximum angle from a nominal position as dictated by the configuration of the swing platform 425 seen in FIGS. 8 and 9 and the geared rack system 1019, 1021 illustrated in FIG. 12. Accordingly, to provide an axial insertion across a distance greater than distance D, the dynamic grippers 440 and 1050 generally must release the guidewire as it reaches a position toward or at an end of its range of motion, move axially rearward and then re-grip the guidewire, and continue the axial insertion. Similarly, to provide a rotation to an angle greater than the maximum angle capability of the swing platform 425 or the geared rack system 1019, 1021, the dynamic grippers 440, 1050 generally must release the guidewire as the swing platform 425 and geared rack system 1019, 1021 reaches a maximum angular travel, allowing the respective systems to move in the opposite rotational direction and re-grip the guidewire to continue rotating the guidewire. The process of gripping and re-gripping an elongate member may occur many times during a given axial or rotational movement command.

Accordingly, it may be necessary to track a user command associated with the drive apparatus 400 and 1000, and selectively adjust the movement of the drive apparatus 400 and 1000 to generally keep a resulting movement of the drive apparatus 400 and 1000 and associated elongated member as close as possible to the commanded movement. In this sense, the challenge is to track a continuous command, i.e., to move or rotate a certain amount, with a discontinuous mechanism having a maximum axial stroke length D or maximum angular rotation that is a smaller magnitude than the commanded movement.

Figure 16:
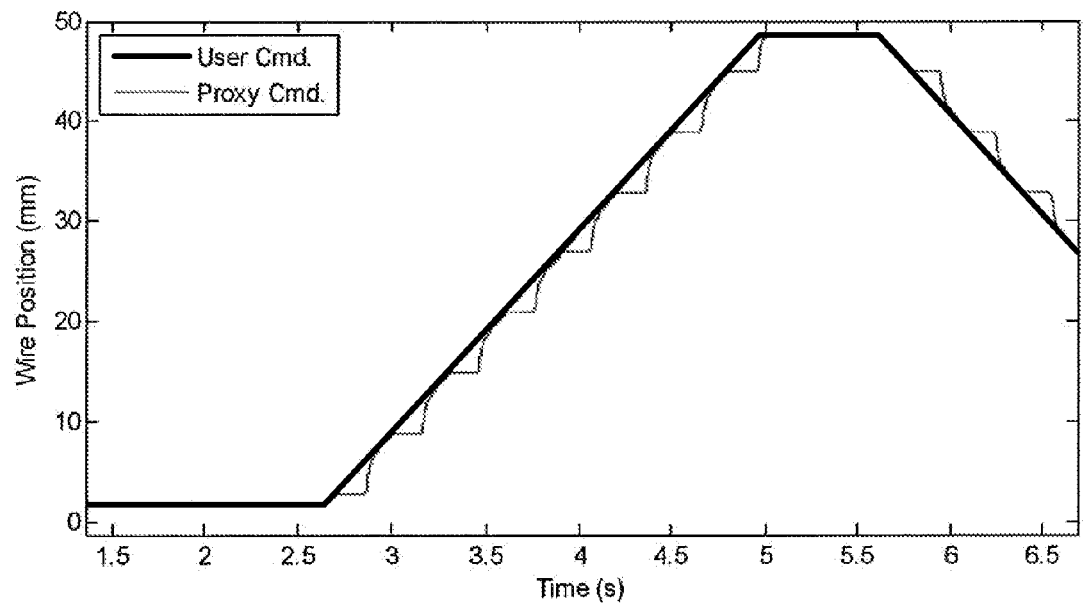
FIG. 16 is a graph illustrating an exemplary proxy command for a drive apparatus.

In one exemplary illustration, an intermediate or proxy command is employed that is internal to a control system, e.g., included in operator workstation 112 or electronics rack 114 of the system 100, or incorporated as part of the drive apparatus 400 or 1000. The controller may generally be aware of the above movement limitations of the mechanism, and may accordingly determine an appropriate movement in response to a given command. Referring now to FIG. 16, an exemplary proxy command is illustrated for an exemplary drive apparatus 400. In this example, the thicker line represents a commanded position provided by the user of the system, while the thinner line illustrates an exemplary proxy command. The proxy command is generally developed internally by the controller based on the user command and the physical realities of the mechanism.

Generally, when the drive apparatus 400, 1000 is away from the end of its range of motion (either axially or rotationally), the proxy command may track the user command tightly. Once the drive apparatus 400, 1000 gets to the end of its range of motion, however, the proxy command may freeze while the mechanism clutches and resets to allow continued driving. When the mechanism is finished with its clutching motion, the proxy command then catches up with the drive command such that the deviation between the commanded position of the wire and the actual wire position is as small as possible for as short a period of time as possible.

Accordingly, the motion of the proxy command may be controlled by a process using two general states for the proxy command: a "freeze" state and a "tracking" state. More specifically, the proxy command may enter the "freeze" state whenever the mechanism under control, i.e., the drive apparatus 400, 1000 indicates that it cannot currently drive. For example, when a user is commanding an insertion motion of 40 millimeters and there is only 20 millimeters remaining the axial range of motion of the drive apparatus 400, 1000, the proxy command may enter the freeze state. Additionally, the freeze state associated with the proxy command may be employed for other purposes, such as when the drive mechanism is deactivated or taken off line, e.g., for diagnostics.

The proxy command spends most of the time in the tracking state. In the tracking state, the proxy command follows the user command with dynamics that generally dictate how the proxy command catches up with the user command when it leaves the freeze state. The dynamics can generally be tuned to achieve whatever behavior is desired for the particular drive apparatus 400, 1000. Depending on the application, the dynamics may provide as smooth and slow a transition as possible, e.g., for procedures where insertion of an elongated member is necessarily very slow; alternatively, the dynamics may provide for as fast and abrupt a transition as possible, or any blend of the two extremes.

In one exemplary illustration, the proxy command is a filtered version of the user command. When the proxy command leaves the freeze state, the filter is reset such that the filter naturally follows a smooth trajectory connecting the proxy command with the user command. Merely as examples, a first order or second order low-pass filter may be employed. In another example, a non-linear filter that includes features such as limiting the maximum speed of the proxy may be employed. A second order filter may advantageously mimic, in terms of the proxy command dynamics, a mass-spring-damper system, i.e., where the proxy can be thought of as a mass which is connected to the user command by a spring and a damper.

Figure 17:
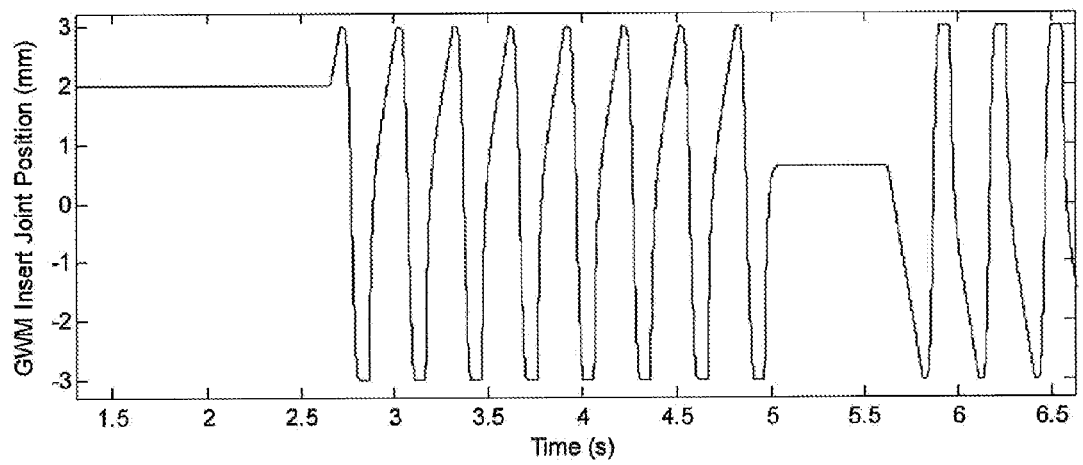
FIG. 17 is a graph illustrating insert joint position for the exemplary proxy command illustrated in FIG. 16.

A proxy command may be mapped to the actual joint commands of the mechanism in any manner that is convenient. In one exemplary illustration of the drive apparatus 400, 1000, the joint command may be reset at the end of every clutching cycle, i.e., when the dynamic grippers 440, 1050 release, move to accommodate additional insertion or rotational motion, and re-grip the elongated member, to be at either the front or the end of the range of motion. The joint command may be incremented by the same amount as the proxy command was incremented every cycle. For example as illustrated in FIG. 17, an actual joint position command that was sent to the drive apparatus 400, 1000 for the same data set as shown in FIG. 16.

In another exemplary illustration, the drive apparatus 400, 1000 may be configured to track a user command for axial motion or rotation of the elongate member by increasing actual velocity of components of the drive apparatus 400, 1000 relative to a velocity expected were releasing/re-gripping not necessary. For example, when there is an expectation that the dynamic grippers 440, 1050 will need to re-grip the elongate member, e.g., due to a commanded motion being beyond the range of motion of the dynamic grippers 440, 1050, the grippers 440, 1050 may increase a velocity of the movement, even in some cases "getting ahead" of the commanded motion. Accordingly, the movement of the elongate member may be preventing from falling behind or falling undesirably far behind a commanded motion. In other words, a drive apparatus 400, 1000 or associated control system may generally compensate for the need to release and re-grip the elongate member by increasing a velocity of a component associated with a commanded motion. In another exemplary illustration, an actual position of an elongated member may be kept within a predetermined range of a commanded movement, i.e., slightly ahead or behind a commanded position, to account for the periodic releasing and re-gripping of the elongate member. Moreover, any velocity or positional adjustments may be performed without intervention by the surgeon, such that the process of releasing and re-gripping the elongate member is generally undetected. In some exemplary approaches, control of any buffer between the commanded position/velocity and actual position/velocity may be quick enough that any positional difference or velocity different resulting from the need to start and stop movement of the elongated member to allow release and re-gripping may generally be imperceptible by the user, e.g., the surgeon.

Figure 18:
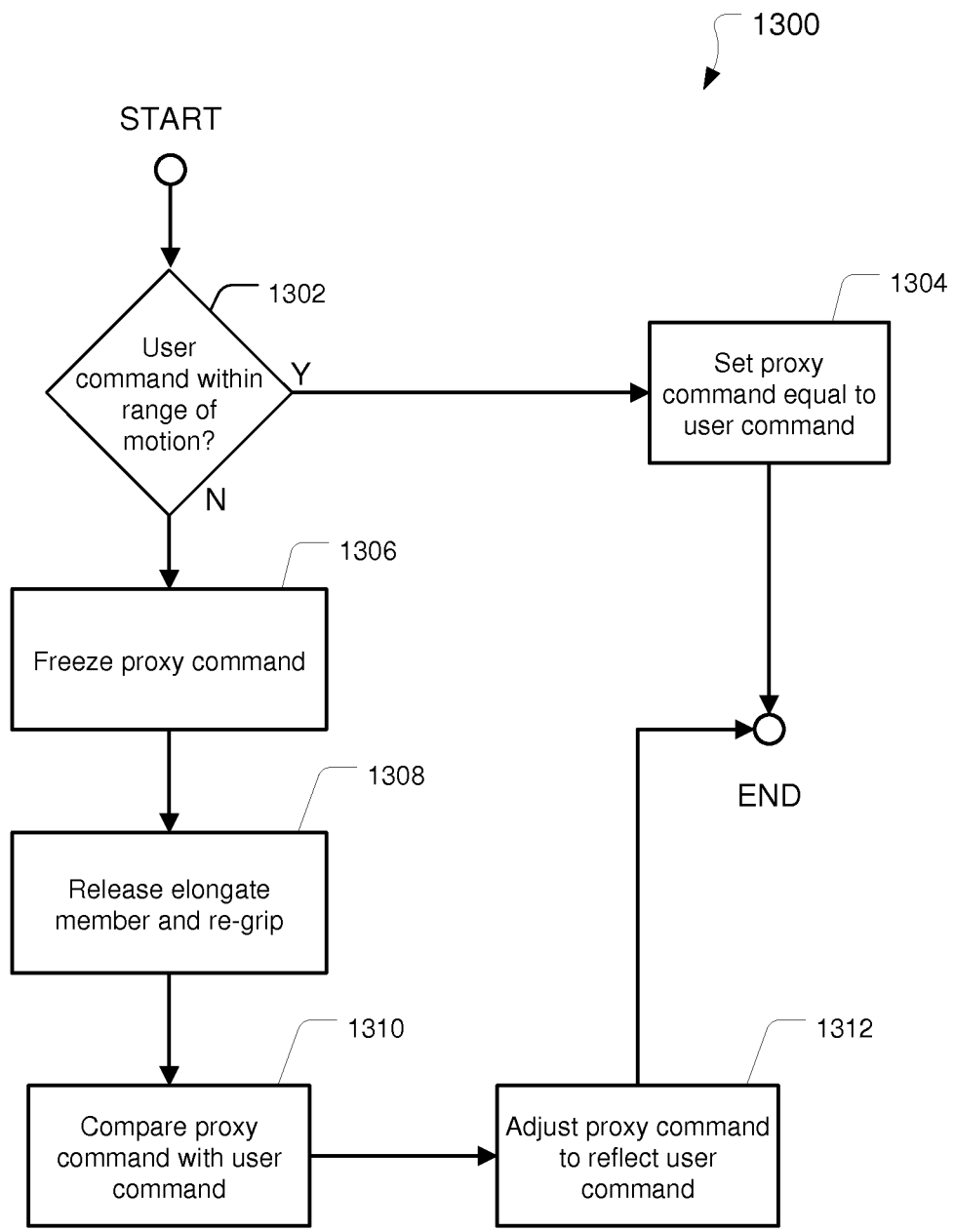
FIG. 18 is a process flow diagram for an exemplary method of providing a generally continuous motion using a discontinuous drive system, e.g., the exemplary drive apparatus illustrated in FIGS. 4-9 and/or FIGS. 10-14.

Turning now to FIG. 18, an exemplary process 1300 for a proxy command is illustrated. The process 1300 is generally begins at block 1302, where the process may query whether a commanded movement of the drive apparatus is within an associated limit to the range of motion.

If a commanded movement is within the range of motion, process 1300 proceeds to block 1304, where the tracking state is set. In other words, if a movement of 40 millimeters is requested by an operator, and 60 millimeters of travel remain in the axial insertion range of the drive apparatus, the proxy command may be equal to the user command.

On the other hand, if the commanded movement is outside the range of motion, then the process 1300 proceeds to block 1306, where the proxy command may enter the freeze state. As noted above the freeze state may allow the drive apparatus 400, 1000 to release and re-grip the elongated member in order to reduce or eliminate the shortfall between the commanded motion and the capability of the drive apparatus 400, 1000. For example, if a rotational movement of 45 degrees is commanded by the user and the maximum rotation available from the current position of the dynamic gripper 440, 1050 is only 35 degrees, then the proxy command may enter the freeze state to allow the dynamic grippers 440, 1050 to be released and rotated to allow greater range of rotational movement.

Proceeding to block 1308, the dynamic grippers 440, 1050 are opened to release the elongate member from their grip, and the dynamic grippers 440, 1050 are then moved to allow greater range of motion and re-grip the elongate member to reduce or eliminate the shortfall between the proxy command and the user command. Process 1300 may then proceed to block 1310.

At block 1310, the commanded position may be compared with the proxy command position, i.e., to determine any shortfall between the new position of the dynamic grippers 440, 1050 and the desired or commanded position.

Proceeding to block 1312, the proxy command may be adjusted with the difference determined at block 1310. As noted above, in some examples the proxy command may be a filtered version of the comparison between the proxy command and the user command, in order to "smooth" the response of the system to differences between the commanded position and the current position of the dynamic grippers. Moreover, the transition may be tuned according to the desired response. A relatively slower transition may be employed in situations where any relatively sudden or relative large movement is especially problematic, while a faster transition may be employed where speed or responsiveness is more essential. Process 1300 may then terminate.

Operator workstation 112, electronics rack 114, drive apparatus 400, and/or drive apparatus 1000 may include a computer or a computer readable storage medium implementing the operation of drive and implementing the various methods and processes described herein, e.g., process 1300. In general, computing systems and/or devices, such as the processor and the user input device, may employ any of a number of computer operating systems, including, but by no means limited to, versions and/or varieties of the Microsoft Windows® operating system, the Unix operating system (e.g., the Solaris® operating system distributed by Oracle Corporation of Redwood Shores, Calif.), the AIX UNIX operating system distributed by International Business Machines of Armonk, N.Y., the Linux operating system, the Mac OS X and iOS operating systems distributed by Apple Inc. of Cupertino, Calif., and the Android operating system developed by the Open Handset Alliance.

Computing devices generally include computer-executable instructions, where the instructions may be executable by one or more computing devices such as those listed above. Computer-executable instructions may be compiled or interpreted from computer programs created using a variety of programming languages and/or technologies, including, without limitation, and either alone or in combination, Java™, C, C++, Visual Basic, Java Script, Perl, etc. In general, a processor (e.g., a microprocessor) receives instructions, e.g., from a memory, a computer-readable medium, etc., and executes these instructions, thereby performing one or more processes, including one or more of the processes described herein. Such instructions and other data may be stored and transmitted using a variety of computer-readable media.

A computer-readable medium (also referred to as a processor-readable medium) includes any non-transitory (e.g., tangible) medium that participates in providing data (e.g., instructions) that may be read by a computer (e.g., by a processor of a computer). Such a medium may take many forms, including, but not limited to, non-volatile media and volatile media. Non-volatile media may include, for example, optical or magnetic disks and other persistent memory. Volatile media may include, for example, dynamic random access memory (DRAM), which typically constitutes a main memory. Such instructions may be transmitted by one or more transmission media, including coaxial cables, copper wire and fiber optics, including the wires that comprise a system bus coupled to a processor of a computer. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

Databases, data repositories or other data stores described herein may include various kinds of mechanisms for storing, accessing, and retrieving various kinds of data, including a hierarchical database, a set of files in a file system, an application database in a proprietary format, a relational database management system (RDBMS), etc. Each such data store is generally included within a computing device employing a computer operating system such as one of those mentioned above, and are accessed via a network in any one or more of a variety of manners. A file system may be accessible from a computer operating system, and may include files stored in various formats. An RDBMS generally employs the Structured Query Language (SQL) in addition to a language for creating, storing, editing, and executing stored procedures, such as the PL/SQL language mentioned above.

In some examples, system elements may be implemented as computer-readable instructions (e.g., software) on one or more computing devices (e.g., servers, personal computers, etc.), stored on computer readable media associated therewith (e.g., disks, memories, etc.). A computer program product may comprise such instructions stored on computer readable media for carrying out the functions described herein.

Slip Detection and Correction

As noted above, an elongated member being used in connection with the drive apparatus 400 may be fed from a feed wheel 406. Similarly, an elongated member associated with drive apparatus 1000 may be fed from a wheel 1002. The feed wheels 406, 1002 may be configured to generally determine whether, when, and/or to what degree the elongated member slips, e.g., axially, during axial motion imparted by the dynamic grippers 440, 1050. For example, while the pads 444a, b of the dynamic gripper 440 and the pads 1003, 1004 of the dynamic gripper 1050 may include relatively high friction surfaces to prevent slippage of the elongated member, at times slippage may nonetheless occur, resulting in inaccuracies in the measured and commanded movements of the drive apparatuses 400 and 1000, respectively. Accordingly, the feed wheels 406, 1002 may be used as a comparison with the movement of the dynamic grippers 440, 1050 to determine when slippage occurs, and to what degree. For example, the feed wheel 406, 1050 may include an optical reader that measures actual rotation of the feed wheels 406, 1002 ultimately determining a length of the elongated member that is actually deployed from the feed wheel 406 at any given time. The actual movement of the elongated member may be compared with the commanded axial movement to determine whether any slippage has occurred, and may subsequently adjust movement of the dynamic grippers 440 accordingly.

In one example, a sensor (not shown in FIGS. 4-14) is within view of the feed wheels 406, 1002 and is outside of the sterile environment such that it need not be replaced after a procedure. More specifically, if the feed wheels 406, 1002 are within the sterile environment, a sensor may be placed on an opposite side of an optically clear section of a sterile drape (not shown in FIGS. 4-14), thereby allowing the sensor to remain outside the sterile environment and reduce the frequency with which the sensor itself must be sterilized or replaced. In another exemplary illustration, both the sensor and the feed wheels 406, 1002 are outside the sterile environment. Merely as examples, a textured surface (not shown) may be positioned on the feed wheels 406, 1002 that is detectable via the sensor. As such, a linear position of an elongate member may be detected using the sensor in any manner that is convenient.

In another exemplary illustration, a sensor outside the sterile field is configured to detect motion of the elongate member and a feed wheel is not necessary. This may be suitable for elongate devices such as catheters that have a braided surface or guidewires that have stripes on the outer extrusion. This detail on the surface of the elongate member may be detected by the sensor to detect motion.

In another exemplary illustration of a slip detection system, one or more idle rollers may be in communication with the elongated member, such that the rollers provide a measure of the length of the elongated member supplied. The measured length may then be compared with the commanded length in order to determine whether any slippage has occurred, allowing the system to adjust subsequent commands from the system.

CONCLUSION

The exemplary illustrations are not limited to the previously described examples. Rather, a plurality of variants and modifications are possible, which also make use of the ideas of the exemplary illustrations and therefore fall within the protective scope. Accordingly, it is to be understood that the above description is intended to be illustrative and not restrictive.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claimed invention.

Accordingly, it is to be understood that the above description is intended to be illustrative and not restrictive. Many embodiments and applications other than the examples provided would be upon reading the above description. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future embodiments. In sum, it should be understood that the invention is capable of modification and variation and is limited only by the following claims.

All terms used in the claims are intended to be given their broadest reasonable constructions and their ordinary meanings as understood by those skilled in the art unless an explicit indication to the contrary in made herein. In particular, use of the singular articles such as "a," "the," "the," etc. should be read to recite one or more of the indicated elements unless a claim recites an explicit limitation to the contrary.

The invention claimed is:

1. A drive apparatus for driving an elongate member into a patient, the drive apparatus comprising:
    a first component mounted to, and fixed rotationally and axially relative to, a support structure and configured to selectively grip the elongate member; and
    a second movable component mounted to, but movable with respect to, the support structure, the second movable component comprising a pair of opposing pads configured to selectively grip and move the elongate member, wherein the pair of opposing pads is axially movable with respect to the support structure to effect axial movement of the elongate member, and wherein the opposing pads are translatable with respect to one another across a limited range of translational motion to effect rotational movement of the elongate member.

2. The drive apparatus of claim 1, wherein the second movable component is configured to simultaneously impart an axial movement and a rotational movement to the elongate member.

3. The drive apparatus of claim 1, wherein the first component comprises an additional pair of opposing pads, wherein the pair of opposing pads of the second component and the additional pair of opposing pads of the first component are each configured to clamp the elongate member therebetween, wherein each of the opposing pads defines an axial length and an axial height, and wherein each of the pairs of opposing pads positioned to open such that a length of the elongate member aligned generally parallel to the axial length of the opposing pads may be loaded into the drive apparatus between the open opposing pads from a direction generally perpendicular to the axial length of the opposing pads.

4. The drive apparatus of claim 1, wherein the opposing pads include a convex contact surface.

5. The drive apparatus of claim 1, wherein the first component and the second movable component are configured to cooperate to continuously grip the elongate member while simultaneously moving the elongate member axially with respect to the support surface.

6. The drive apparatus of claim 1, wherein the second movable component is configured to travel axially with respect to the first component over a maximum axial stroke length; and
    wherein the first component and the second movable component are configured to cooperate to continuously grip the elongate member while simultaneously moving the elongate member with respect to the first component through a first distance axially, wherein the first distance is greater than the maximum axial stroke length.

7. The drive apparatus of claim 1, wherein the first component and the second movable component are configured to cooperate to continuously grip the elongate member while simultaneously rotating the elongate member with respect to the support surface.

8. The drive apparatus of claim 1, wherein the second movable component is configured to rotate with respect to the first component over a maximum radial stroke angle; and
   wherein the first component and the second movable component are configured to cooperate to continuously grip the elongate member while simultaneously rotating the elongate member with respect to the first component through a first angle, wherein the first angle is greater than the maximum radial stroke angle.

9. The drive apparatus of claim 1, further comprising a disposable portion defining a sterile barrier positioned between the first component and the second movable component and the elongate member.

10. The drive apparatus of claim 1, wherein the drive apparatus is configured to detect a slipping of the elongate member with respect to a drive command.

11. A drive apparatus for driving an elongate member into a patient, the drive apparatus comprising:
   an elongate member;
   a first gripping device fixed rotationally and axially with respect to a support surface, the first gripping device configured to selectively grip the elongate member; and
   a second gripping device mounted to the support surface for rotation and axial travel with respect to the support surface, the second gripping device comprising a pair of opposing gripping pads configured to selectively grip the elongate member and selectively move axially together with respect to the support surface and translationally relative to each other to effect axial movement and rotational movement, respectively, of the elongate member with respect to the support surface, the second gripping device being confined to a range of motion;
   wherein the second gripping device is configured to move the elongate member a distance having a magnitude greater than the range of motion.

12. The drive apparatus of claim 11, wherein the second gripping device is configured to rotate the elongate member with respect to the support surface and move the elongate member axially with respect to the support surface simultaneously.

13. The drive apparatus of claim 11, wherein each of the opposing gripping pads defines an axial length and an axial height, and wherein the opposing gripping pads are positioned to open such that a length of the elongate member aligned generally parallel to the axial length of the opposing gripping pads may be loaded into the drive apparatus between the open opposing gripping pads from a direction generally perpendicular to the axial length of the opposing gripping pads.

14. The drive apparatus of claim 11, wherein the first and second gripping devices are configured to cooperate to continuously grip the elongate member while simultaneously moving the elongate member axially with respect to the support surface.

15. The drive apparatus of claim 14, wherein the second gripping device is configured to travel axially with respect to the support surface over a maximum axial stroke length; and
   wherein the first and second gripping devices are configured to cooperate to continuously grip the elongate member while simultaneously moving the elongate member through a first distance axially with respect to the support surface, the first distance greater than the maximum axial stroke length.

16. The drive apparatus of claim 11, wherein the first and second gripping devices are configured to cooperate to continuously grip the elongate member while simultaneously rotating the elongate member with respect to the support surface.

17. The drive apparatus of claim 16, wherein the second gripping device is configured to rotate with respect to the support surface over a maximum radial stroke angle; and
   wherein the first and second gripping devices are configured to cooperate to continuously grip the elongate member while simultaneously rotating the elongate member with respect to the support surface through a first angle, the first angle greater than the maximum radial stroke angle.

18. The drive apparatus of claim 11, wherein the elongate member includes one of a catheter sheath or a guide wire.

* * * * *